US007856320B2

(12) United States Patent
Najarian

(10) Patent No.: US 7,856,320 B2
(45) Date of Patent: *Dec. 21, 2010

(54) SYSTEMS FOR GENE EXPRESSION ARRAY ANALYSIS

(75) Inventor: Kayvan Najarian, Concord, NC (US)

(73) Assignee: University of North Carolina at Charlotte, Charlotte, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/273,687

(22) Filed: Nov. 14, 2005

(65) Prior Publication Data

US 2006/0074566 A1    Apr. 6, 2006

Related U.S. Application Data

(62) Division of application No. 10/812,726, filed on Mar. 30, 2004, now Pat. No. 6,996,476.

(60) Provisional application No. 60/518,505, filed on Nov. 7, 2003.

(51) Int. Cl.
*C12Q 1/68* (2006.01)
*C07H 21/04* (2006.01)
*G01N 33/48* (2006.01)

(52) U.S. Cl. ............................ 702/19; 435/6; 536/23.1; 702/20

(58) Field of Classification Search ................... None
See application file for complete search history.

(56) References Cited

U.S. PATENT DOCUMENTS

| 6,090,555 | A | 7/2000 | Fiekowsky et al. |
| 6,144,388 | A | 11/2000 | Bornstein |
| 6,222,093 | B1 | 4/2001 | Marton et al. |
| 6,263,287 | B1 | 7/2001 | Zheng et al. |
| 6,303,301 | B1 | 10/2001 | Mack |
| 6,453,241 | B1 | 9/2002 | Bassett, Jr. et al. |
| 6,642,887 | B2 | 11/2003 | Owechko |
| 6,996,476 | B2 | 2/2006 | Najarian |
| 2008/0294613 | A1* | 11/2008 | Iyer et al. ...................... 707/4 |

OTHER PUBLICATIONS

American Heritage Dictionary of the English Language, definition for "carrier wave." Printed from the Internet at <http://www.bartleby.com/61/79/C0127900.html> on Aug. 31, 2008.*

Dictionary efination for the word "Device." Merriam-Webster Online. Printed from <http://www.merriam-webster.com/dictionary/device> on Feb. 16, 2009.*

Darvish, A., et al., "System identification and Nonlinear Factor Analysis for Discovery and Visualization of Dynamic Gene Regulatory Pathways," Proceedings of the 2005 IEEE Symposium on Computational Intelligence in Bioinformatics and Computational Biology, San Diego, CA, Nov. 2005.

Back, A. D. et al. "A First Application of Independent Component Analysis to Extracting Structure From Stock Returns,"Int. J. Neural Syst., 8:5, Oct. 1997, 1-16.

Bassett, D. E. Jr. et al., "Gene Expression Informatics—It's All in Your Mine," Nat Genet. Jan. 1999, 21 (1 Suppl):51-5.

Blohm, D. H. et al., "New Developments in Microarray Technology,"Curr. Opin. Biotechnol., 12:41-47, 2001.

Bowtell, D. D.L., "Options Available—From Start to Finish—for Obtaining Expression Data by Microarray," Nat. Genet. Jan. 1999, 21 (1 Suppl):25-32.

Brazma, A. et al., "Gene Expression Data Analysis," FEBS Lett. Aug. 25, 2000 480(1):17-24.

Cheung, V. G. et al., "Making and Reading Microarrays," Nat Genet. Jan. 21, 1999 (1 Suppl):15-9.

Cho, R. J., et al., "A Genome-Wide Transcriptional Analysis of the Mitotic Cell Cycle," Molecular Cell, 2:65-73, Jul. 1998.

Darvish, A. et al., "A Hierarchical System Identification Technique for Modeling and Analysis of Dynamic Pathways," Bioinformatics, May 2004.

Darvish, A. et al., "Discovering Dynamic Regulatory Pathway by Applying an Auto Regressive Model to Time Series DNA Microarray Data," IEEE Engineering in Medicine and Biology Society (IEEE/EMBS), Sep. 1-5, 2004.

Darvish, A. et al., "A New Hierarchical Method for Identification of Dynamic Regulatory Pathways from Time-Series DNA Microarray Data," Proceedings of the 2005 IEEE Symposium on Computional Intelligence in Bioinformatics and Computatuinal Biology, San Diego, U.S.A., Nov. 2005.

Devaux, F. et al., "Transcriptomes, Transcription Activators and Microarrays," FEBS Lett. Jun 8, 2001 498(2-3):140-4.

Dudoit, S., "Statistical Methods and Software for the Analysis of DNA Microarray Experiments," Bioinformatics and Computational Biology Workshop, Foundation BBVA, Madrid, Apr. 25-26, 2002.

Duggan, D. J. et al., "Expression Profiling Using cDNA Microarrays," Nat Genet. Jan. 21, 1999 (1 Suppl):10-4.

Greenberg, S. A., "DNA Microarray Gene Expression Analysis Technology and Its Application to Neurological Disorders," Neurology, Sep. 11, 2001; 57(5):755-61.

Hacia, J. G., "Resequencing and Mutational Analysis Using Oligonucleotide Microarrays," Nat Genet. Jan. 21, 1999(1 Suppl):42-7.

Harkin, D. P., "Uncovering Functionally Relevant Signaling Pathways Using Microarray-Based Expression Profiling," Oncologist. 2000; 5(6):501-7.

(Continued)

*Primary Examiner*—Shubo (Joe) Zhou
(74) *Attorney, Agent, or Firm*—Kilpatrick Stockton LLP

(57) ABSTRACT

Disclosed are methods and systems for applying independent component analysis (ICA) and other advanced signal processing techniques to automatically identify an optimal number of independent gene clusters and to efficiently separate gene expression data into biologically relevant groups. Embodiments of the methods and systems of the present invention provide an interface that allows the user to review the results at various stages during the analysis, thereby optimizing the type of analysis performed for a specific experiment. Also disclosed are methods and systems to mathematically define the relationship for gene expression within a group of interrelated genes.

42 Claims, 8 Drawing Sheets

OTHER PUBLICATIONS

Hegde, P. et al., "*A Concise Guide to cDNA Microarray Analysis-II*," Biotechniques, 29(3), Sep. 2000,548-562.

Holloway, A. J. et al., "*Options Available—From Start to Finish—for Obtaining Data from DNA Microarrays II*," Nat Genet. 32, Dec. 2002,481-9 (1 Suppl).

Hori, G. et al., "*Blind Gene Classification Based on ICA or Microarray Data*," ICA 2001 Meeting, San Diego, U. S. A., pp. 332-336, 2001.

Hughes, T. R. et al, "*DNA Microarrays for Expression Profiling*," Curr. Opin. Chem. Biol., 5:21-25, 2001.

Jolliffe, I. T, *Principal Component Analysis*, New York: Springer-Verlag, 1986.

Lee, S. I. et al., "Application of Independent Component Analysis to Microarrays," Genome Biology, vol. 4, No. R76, Oct. 24, 2003.

Liebermeister, W., "*Linear Modes of Gene Expression Determined by Independent Component Analysis*," Bioinformatics, 18:1, pp. 51-60, 2002.

Makeig, S. et al., "*Independent Component Analysis of Electroencephalographic Data*," Proceedings of the Advances in Neural Information Processing Systems 8, Eds., Touretzky et al, MIT Press, pp. 145-151, 1996.

Nadon, R. et al., "*Statistical Issues with Microarrays: Processing and Analysis*," Trends in Genet. May 2002;18(5):265-71.

Najarian, K. et al., "*Independent Component Analysis and Scoring Function Based on Protein Interactions*," Proceedings of IEEE International Conference Intelligent Systems, Jun. 2004.

Najarian, K. et al., "*A Unified Nonlinear Signal Processing and System Identification Approach to Dynamic Pathway Identification from DNA Microarray Data*", Poster Presented at Proceedings of BISTI 2003 Symposium on "Digital Biology: The Emerging Paradigm", Washington, D.C., Nov. 6-7, 2003.

Pajunen, P. et al., "*Nonlinear Blind Source Separation by Self-Organizing Maps*," Proc. Int. Conf. On Neural Information Processing, Hong Kong, pp. 1207-1210, 1996.

Quackenbush, J., "*Computational Analysis of Microarray Data*," Nat. Rev. Genet. Jun. 2001;2(6):418-27.

Raychaudhuri, S. et al., "*Basic Microarray Analysis: Grouping and Feature Reduction*," Trends in Biotechnology, vol. 19, No. 5, pp. 189-193, May 2001.

Schulze, A. et al., "*Navigating Gene Expression Using Microarrays—A Technology Review*", Nature Cell Biology, 3:E190-E195, Aug. 2001.

Sherlock, G., "Analysis of Large-Scale Gene Expression Data," Current Opinion in Immunology, 12:201-205, 2000.

Sherlock, G., "*Analysis of Large-Scale Gene Expression Data*," Briefings in Bioinform. Dec. 2001;2(4):350-62.

Southern, E. et al., "*Molecular Interactions on Microarrays*," Nat Genet. Jan. 1999;21(1 Suppl):5-9.

Stone, J. V. et al., "*Spatiotemporal Independent Component Analysis of Event-Related fMRI Data Using Skewed Probability Density Functions*,"Neuroimage, 15:407-421, 2002.

Torkkola, K. et al., "*Self-Organizing Maps in Mining Gene Expression Data*," Information Sciences, 139:79-96, 2001.

Toronen, P. et al. "*Analysis of Gene Expression Data Using Self-Organizing Maps*," FEBS Lett. May 21, 1999;451(2)142-6.

Vigario, R. N., "*Extraction of Ocular Artefacts from EEG Using Independent Component Analysis*," Electroenceph. Clin. Neurophysiol., 103:395-404, 1997.

Wu, T. D., "*Analysing Gene Expression Date from DNA Microarrays to Identify Candidate Genes*," J Pathol. Sep. 2001;195(1):53-65.

Yeung, K. Y. et al., "*Principal Component Analysis for Clustering Gene Expression Data*," Bioinformatics, Sep. 2001;17(9):763-74.

Ziv Bar-Joseph et al., "*Comparing the Continuous Representation of Time-Series Expression Profiles to Identify Differentially Expressed Genes*," Proc. Natl. Acad. Sci., U. S. A., 100 (18):10146-10151, 2003.

"Microarray Explorer Tool for Data Mining Gene Expression Patterns," web page at http://maexplorer.sourceforge.net/ as available via the internet and printed on Nov. 2, 2003.

"My Microarray Software Comparison—Image Analysis Software," web page at http://ihome.cuhk.edu.hk/~b400559/arraysoft_image.html as available via the internet and printed on Nov. 2, 2003.

"My Microarray Software Comparison—Data Mining Software," web page at http://ihome.cuhk.edu.hk/~b400559/arraysoft$_{13}$mining.html as available via the internet and printed on Nov. 2, 2003.

"My Microarray Software Comparison—Data Preprocessing Software," web page at http://ihome.cuhk.edu.hk/~b400559/arraysoft_preprocess.html as available via the internet and printed on Nov. 2, 2003.

"My Microarray Software Comparison—Statistics Software and Technical Programming Languages," web page at http://ihome.cuhk.edu.hk/~b400559/arraysoft_statistics.html as available via the internet and printed on Nov. 2, 2003.

"My Microarray Software Comparison," web page at http://ihome.cuhk.edu.hk/~b400559/arraysoft.html as available via the internet and printed on Nov. 2, 2003.

"My Microarray Software Comparison—Data Mining Software (Turnkey/Enterprise System)," web page at http://ihome.cuhk.edu.hk/~b400559/arraysoft_mining_turnkey.html as available via the internet and printed on Nov. 2, 2003.

"My Microarray Software Comparison—Data Mining Software (Comprehensive Software)," web page at http://ihome.cuhk.edu.hk/~b400559/arraysoft_mining_comprehensive.html as available via the internet and printed on Nov. 2, 2003.

"My Microarray Software Comparison—Data Mining Software (Extension of Existing Data Mining Software)," web page at http://ihome.cuhk.edu.hk/~b400559/arraysoft_mining_extension.html as available via the internet and printed on Nov. 2, 2003.

"My Microarray Software Comparison—Network/pathway Reconstruction and Analysis Software," web page at http://ihome.cuhk.edu.hk/~b400559/arraysoft_pathway.html as available via the internet and printed on Nov. 2, 2003.

"My Microarray Software Comparison—R Packages for Microarray Analysis," web page at http://ihome.cuhk.edu.hk/~b400559/arraysoft_rpackages.html as available via the internet and printed on Nov. 2, 2003.

Affymetrix web page at http://www.biospace.com/company_profile.cfm?CompanyID=1271 as available via the internet and printed on Feb. 23, 2004.

An IMS Mini-Meeting on Imaging, Classification, and Clustering, Department of Statistics, University of Florida, Jan. 11-12, 2002.

Bioconductor, web page at http://www.bioconductor.org/top.html as available via the internet and printed on Nov. 2, 2003.

BioSieve Products—Microarray Data Analysis Software at http://www.biosieve.com/product.html as available via the internet and printed on Nov. 2, 2003.

Cluster Analysis on Microarray Data at web page http://www.cs.bufalo.edu/~djiang3/cluster.html as available via the internet and printed on Nov. 10, 2003.

Clustering Software web page at http://genetics.stanford.edu/~sherlock/cluster.html as available via the internet and printed on Nov. 2, 2003.

Cytoscape web page at http://www.cytoscape.org/ as available via the internet and printed on Nov. 2, 2003.

Engene Gene-Expression Data Processing and Exploratory Data Analysis web page at http://www.engene.cnb.uam.es/ as available via the internet and printed on Nov. 2, 2003.

Expression Profiler web page at http://ep.ebi.ac.uk/EP/ as available via the internet and printed on Nov. 2, 2003.

FAST-ICA: HUT—CIS web page at http://www.cis.hut.fi/projects/ica/fastica/ as available via the internet and printed on Feb. 16, 2004.

Gene Expression Pattern Analysis Suite (GEPAS) at http://gepas.bioinfo.cnio.es/tools.html as available via the internet and printed on Nov. 2, 2003.

Gene Network Sciences, Simulating Life for Drug Discovery web page at http://www.gnsbiotech.com/biomine.shtml as available via the internet and printed on Nov. 2, 2003.

Gene Network Sciences, BioMine™ 1.0, web page at http://www.gnsbiotech.com/biomine.shtml as available via the internet and printed on Nov. 2, 2003.

GeneMaths: GenExplore—High Throughput Analysis of Gene Expression Data at http://www.applied-maths.com/ge/ge_fr2.htm as available via the internet and printed on Nov. 2, 2003.

Genesis Description at http://genome.tugraz.at/Software/Genesis/Description.html as available via the internet and printed on Nov. 2, 2003.

Genotypic Technology: Genowizard—Microarray Data Analysis System web page at http:///www.genotypictech.com/genowizard.html as available via the internet and printed on Nov. 2, 2003.

HumanaNow, "Statistical Issues in cDNA Microarray Data Analysis," web page at http://biomed.humanapress.com/ChapterDetail.pasp?isbn=1-59259-364-X&ccode=1-5925 as available via the internet and printed on Nov. 2, 2003.

IFMBE News: Maide Bucolo, Sep. 2002 web page at http://ifmbe-news.iee.org/ifmbe-news/sept2002/bucolo.html as available via the internet and printed on Nov. 10, 2003.

Bioinformatics Graz-MPI Swarm Description http://genome.tugraz.at/Software/PathwayEditor/Description.html as available via the internet and printed on Nov. 2, 2003.

Partek Pattern Recognition Software web page at http://www.partek.com/html/products/products.html as available via the internet and printed on Nov. 2, 2003.

Rosetta Features web page at http://rosetta.lcb.uu.se/general/features.html as available via the internet and printed on Nov. 2, 2003.

SAS, web page at http://www.sas.com/contact/intro.html as available via the internet and printed on Feb. 16, 2004.

Silicon Genetics Products: GeneSpring; The Industry Leader web page at http://www.silicongenetics.com/cgi/SiG.cgi/Products/GeneSpring/index.smf as available via the internet and printed on Nov. 2, 2003.

The MathWorks: MATLAB and Simulink for Technical Computing, web page at http://www.mathworks.com/company/contact.shtml as available via the internet and printed on Feb. 16, 2004.

Kauffman, "The Origins of Order: Self Organization and Selection in Evolution," Oxford University Press, New York: 1993.

Lee, "Application of independent component analysis to microarrays," Genome Biology, 2003, 4: R76.1-R76.21.

Martoglio et al., "A decomposition model to track gene expression signatures: preview on observer-independent classification of ovarian cancer," Bioinformatics, 2002, 18: 1617-1624.

Notice of Allowance and Fees Due mailed Jul. 15, 2005 for U.S. Appl. No. 10/812,726.

Office Communication mailed Dec. 9, 2005 for U.S. Appl. No. 10/812,726.

*Ex Parte Quayle* Office Action mailed Feb. 9, 2005 for U.S. Appl. No. 10/812,726.

Office Action mailed Sep. 9, 2004 for U.S. Appl. No. 10/812,726.

Amendment and Response Under *Ex Parte Quayle* for U.S. Appl. No. 10/812,726 sent to USPTO on Apr. 6, 2005.

Request for Certificate of Correction of Patent for Applicant's Mistake (37 C.F.R. § 1.323) and for PTO Mistakes (37 C.F.R. § 1.322(a)) for U.S. Appl. No. 10/812,726 sent to USPTO on Oct. 3, 2006.

Communication to USPTO for U.S. Appl. No. 10/812,726 faxed to USPTO on Oct. 7, 2005.

Darvish, A. et al., "System Identification and Independent Factor Analysis for Estimation of Dynamic Gene Regulatory Networks," Oxford University Press 2005.

Akutsa, T. et al., Identification of Genetic Networks from a Small Number of Gene Expression Patterns under the Boolean Network Model, Pacific Symposium on Biocomputing, 4:17-28, 1999.

Arkin, A. et al., Stochastic Kinetic Analysis of Developmental Pathway Bifurication in Phage λ-Infected *Escherichia coli* Cells, Genetics, 149:1633-1648, 1998.

Eisen et al., "Cluster Analysis and Display of Genome-Wide Expression Patterns," Proc. Natl. Acad. Sci., USA., 95:14863-14868, 1998.

Gat-Viks et al., "Chain Functions and Scoring Functions in Genetic Networks," Bioinformatics, vol. 19, Supp. 1, i108-i117, 2003.

Glover, D., "DNA Cloning: A Practical Approach," vol. I, 1985.

Goodwin, B. et al., "Is Morphogenesis an Intrinsically Robust Process?" J. Theor. Biol., 163:135-144, 1993.

Hartemink et al., "Combining Location and Expression Data for Principled Discovery of Genetic Regulatory Network Models," Pac. Symp. Biocomput., 437-439, 2002.

Kholodenko, B. et al., "Untangling the wires: a strategy to trace functional interactions in signaling and gene networks," Proc. Natl. Acad. Sci., USA, 99:2841-12846, 2002.

Lappalainen, H. et al., Bayesian Non-linear Component Analysis by Multi-Layer Perceptrons, in:Advances in Independent Component Analysis, Mark Girolami ed., Sprnger, 93-121, 2000.

Maniatis, T. et al., "Molecular Cloning: A Laboratory Manual," 1982.

Solazzi, M. et al., "Spline Neural Networks for Blind Separation of Post-Nonlinear-Linear Mixtures," IEEE Transactions on Circuits and Systems I: Regular Papers, 51(4):817-829, 2004.

Somogyi, R. et al., "The Gene Expression Matrix: Towards the Extraction of Genetic Network Architectures," Nonlinear Analysis, Theory, Methods & Applications, vol. 30, No. 3, pp. 1815-1824, 1997.

Yang, H.H. et al., "Information-Theoretic Approach to Blind Separation of Sources in Non-Linear Mixture," Signal Processing, 64, 291-300, 1998.

Yeung, M.K.. et al., "Reverse Engineering Gene Networks Using Singular Value Decomposition and Robust Regression," Proc. Natl. Acad. Sci., USA, 9:6163-6168, 2002.

Yuh, C.H. et al., "Genomic Cis-Regulatory Logic: Experimental and Computational Analysis of a Sea Urchin Gene," Science, 279:1896-1902, 1998.

United States Patent and Trademark Office, Office Action, U.S. Appl. No. 11/603,591, mailed Jun. 23, 2010.

* cited by examiner

Cluster 1: Early G1 Phase

SWI4  
◊ actual  * estimated

CDC46  
◊ actual  * estimated

Cluster 2: Early G2 Phase

SWE1  
◊ actual  * estimated

GIN4  
◊ actual  * estimated

Cluster 3: S Phase

NUD1  ◊ actual  * estimated

CIN8  ◊ actual  * estimated

Cluster 4: G2 Phase

CSE4  ◊ actual  * estimated

ELM1  ◊ actual  * estimated

SYSTEMS FOR GENE EXPRESSION ARRAY ANALYSIS

RELATED APPLICATIONS

This application is a divisional of U.S. patent application Ser. No. 10/812,726, filed Mar. 30, 2004 now U.S. Pat. No. 6,996,476, and claims priority to U.S. Provisional Application Ser. No. 60/518,505, filed Nov. 7, 2003. The disclosure of U.S. Provisional Application Ser. No. 60/518,505 is hereby incorporated by reference in its entirety herein.

NOTICE OF COPYRIGHT PROTECTION

A section of the disclosure of this patent document and its figures contain material subject to copyright protection. The copyright owner has no objection to the facsimile reproduction by anyone of the patent document, but otherwise reserves all copyright rights whatsoever.

FIELD OF INVENTION

The present invention relates to analyzing gene expression. More particularly, the present invention relates to systems and methods for analyzing genes and their expression profiles based upon array analysis.

BACKGROUND

DNA sequence data has been rapidly accruing. Still, completion of the Human Genome Project and other genome sequencing projects has shown that DNA sequence data provides only a partial picture of gene function. What is missing is a full understanding of what factors trigger gene expression, as well as a full understanding of the temporal profile of gene expression, and how particular genes may interact with each other.

Recently, DNA microarrays have become a valuable tool for exploring gene expression. DNA microarrays may be formed using fragments of genomic DNA, DNA pools generated by cloning or other amplification and/or selection techniques, or even short stretches of DNA known as oligonucleotides.

A single microarray chip may yield expression profiles for thousands of genes. Still, the data provided by such arrays, while fairly straightforward to generate, may provide significant challenges with respect to analysis. Often, in order for this type of research to be most productive, thousands of data points need to be directly compared in a single experiment. For example, in some cases it may be important to compare gene expression profiles over time, thus multiplying the number of data points generated from a single array by the number of time points measured.

Also, for many studies, the goal is to determine the cause-and-effect relationship by which particular genes are expressed. For example, expression of one gene may inhibit, enhance, or have no effect on the expression of a second gene. Alternatively, expression of one gene may influence another gene, but there may be a lag period. Also, the expression profile for a particular gene may be modified by changes in the environment, such as a physical changes in the cell or as a result of chemical signals inducing or inhibiting expression. Extracting this type of information from array data can be a challenging task, especially when the identity and function of most of the genes under study is unknown.

To date, several methods have been developed to analyze array data including K-Means, principal component analysis (PCA), and self-organizing maps (SOM). None of the techniques currently being used are completely optimized for this type of analysis, however.

A main objective of microarray data analysis is to identify the "independent" clusters of genes, such that the genes belonging to the gene cluster have similar expression patterns that may be involved in, or required for, a specific physiological response. For example, it is expected that there may be one subset of genes required for cholesterol metabolism, a second subset involved in the immune response, and yet another subset of genes involved in the development of cancer. It would be of interest to identify these pools of genes to develop a better understanding of these processes and to identify targets for potential therapeutic agents.

In most existing microarray processing technologies, the process of selecting the number of gene groups that describes the number of independent pathways is left up to the user. Incorrectly selecting the number of independent groups can skew the analysis such that vastly different results are generated depending upon how many independent gene groups are assumed.

Thus, what is needed is methods and systems to analyze genomic expression data in an effective manner. Such systems and methods preferably will comprise computerized statistical techniques. In this way, the data may be analyzed in a way that provides meaningful results. Also, what is needed is a way to describe the interrelationship between genes in a group.

SUMMARY

Embodiments of the present invention comprise methods and systems for gene expression array analysis. For example, one embodiment of the present invention comprises a gene microarray processing technology for extracting biologically meaningful results from microarray data. Another embodiment comprises a method for the analysis of gene expression data that clusters genes having related expression profiles into optimally defined independent groups, without a need for any assumptions regarding the size and/or numbers of clusters. An example embodiment of the present invention uses optimized independent component analysis to cluster genes into physiologically relevant groups based on their expression profiles. In addition, methods and systems to correlate the expression patterns of the gene groups to observed biological changes, and to determine the interrelationship between genes within a group, are described. Yet another embodiment of the present invention comprises isolated nucleic acid molecules comprising sequences comprising a gene expression profile and/or gene function as identified using iterative independent component analysis.

BRIEF DESCRIPTION OF THE FIGURES

FIG. 5 shows predicted and actual expression patterns for known genes expressed in various phases of the yeast cell cycle in accordance with an embodiment of the present invention. Expression profiles for genes at various points of the yeast cell cycle are as follows: Panel A. Early G1; Panel B, Early G2; Panel C, S phase; Panel D, G2 phase; and Panel E, M phase. In each graph, the x axis is the time of cell growth in hours and the y-axis is the level of gene expression measured using a hybridization based assay. The actual genes assayed are listed below each graph. Thus.

DETAILED DESCRIPTION

Figure 1:
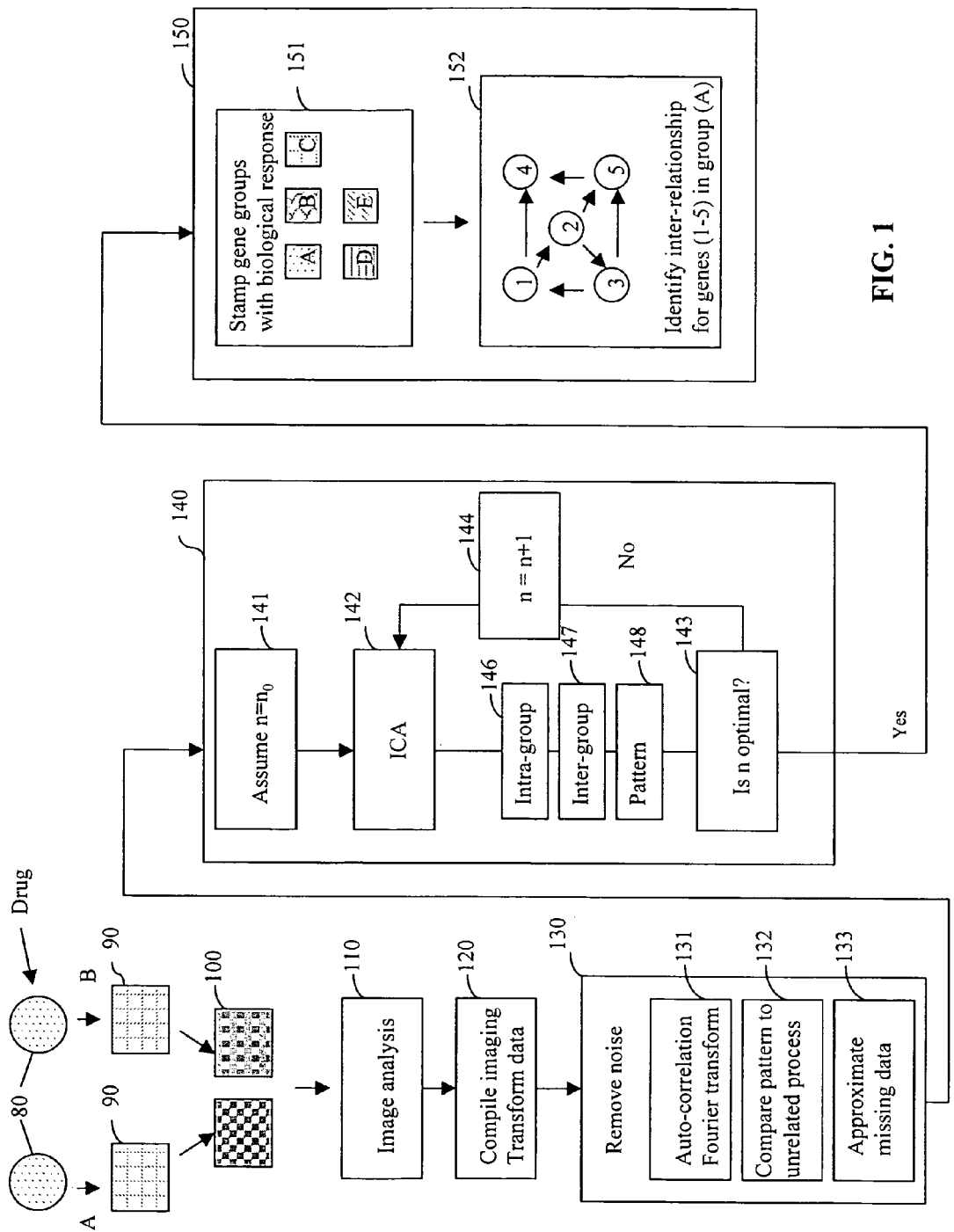
FIG. 1 shows a schematic diagram of a method for array analysis in accordance with an embodiment of the present invention.

The present invention provides systems and methods for the analysis of gene expression profiles. Using microarray analysis, an array having thousands of data points may be used to describe genes related to a specific biological or physiological process.

Certain embodiments of the present invention comprise methods and systems that efficiently address the analysis of gene array data to identify independent clusters of gene expression profiles and to describe and quantify interrelated pathways for genes within a cluster. The method may be used to identify gene clusters and the interaction of particular gene groups with various environmental factors such as the concentration of a particular drug or chemical, pH, osmolarity, or temperature. The method may also be used to identify gene clusters and the interaction of genes within a group that are required for a particular biological response, such as the healing process, metabolism of certain compounds, the immune response, or cancer. One embodiment of the present invention comprises a computer-implemented method which may be used with a standard laboratory personal computer (PC) employing statistical software common in the art. Also described are systems using the methods of the present invention that may be used in conjunction with imaging systems and data processing systems typically used for analysis of DNA microarrays.

In one embodiment, the present invention comprises a computer-implemented method for analyzing gene expression for at least one cell type from data comprising a plurality of measured signals wherein the method comprises using iterative independent component analysis (ICA) to identify an optimum number of independent clusters into which the data may be grouped. For example, in an embodiment, the method comprises a computer-implemented method for analyzing gene expression wherein the method comprises the steps of: (a) compiling data comprising a plurality of measured gene expression signals into a form suitable for computer-based analysis; and (b) analyzing the compiled data using iterative independent component analysis (ICA), wherein analyzing comprises identifying an optimum number of independent clusters into which the data may be grouped.

Another embodiment of the present invention comprises a method to determine the interaction of genes that are involved in the same biological pathway or response. An example embodiment comprises a computer-implemented method for analyzing gene expression comprising: (a) compiling data comprising a plurality of measured gene expression signals into a form suitable for computer-based analysis; (b) applying iterative independent component analysis to cluster the data into an optimal number, n, of independent groups, wherein genes in one independent group comprise expression profiles that are, on a statistical basis, substantially independent of the expression profiles for genes in the other groups; and (c) determining if there is a cross-correlation between at least two genes within a cluster group, wherein a positive cross-correlation comprises the situation in which the expression of one gene in the group is statistically correlated with the expression of a second gene in the same group. In an embodiment, for positively correlated genes, the expression of one of the genes is dependent upon expression of the other gene. Also, in an embodiment, noise is removed from the data prior to the step of applying iterative independent component analysis to the data.

The present invention also comprises computer-readable media which may provide such methods to a plurality of users. Thus, in an embodiment, the invention comprises a computer-readable medium on which is encoded programming code for analyzing gene expression wherein the programming code applies iterative independent component analysis (ICA) to data comprising a plurality of measured signals to identify an optimum number of independent clusters into which the data may be grouped.

A computer-readable medium according to the present invention may include software to evaluate the interaction of genes that are involved in the same biological pathway or response. Thus, in an embodiment, the present invention comprises a computer-readable medium on which is encoded programming code for analyzing gene expression comprising code for: (a) removing noise from the data; (b) using iterative independent component analysis to cluster data comprising a plurality of measured gene expression signals into an optimal number, n, of independent groups, wherein genes in one independent group comprise expression profiles that, on a statistical basis, are substantially independent of the expression profiles for genes in the other groups; and (c) determining if there is a cross-correlation between at least two genes within a cluster group, wherein a positive cross-correlation comprises the situation in which the expression of one gene in the group is statistically correlated with the expression of a second gene in the same group. In an embodiment, for positively correlated genes, the expression of one of the genes is dependent upon expression of the other gene. In an embodiment, the programming code further comprises code that compiles the data into a form suitable for computer analysis.

Embodiments of the present invention further comprise systems comprising iterative independent component analysis for gene expression array analysis. For example, in an embodiment, the present invention comprises a system for analyzing gene expression comprising a computer-readable medium on which is encoded programming code for using iterative independent component analysis (ICA) to identify an optimum number of independent clusters into which data comprising a plurality of measured gene expression signals may be grouped and a computer for executing said programming code.

In yet another embodiment, the present invention comprises an isolated nucleic acid molecule comprising a sequence having a gene expression profile and/or gene function as identified using iterative independent component analysis. In an embodiment, the isolated nucleic acid sequence may comprise DNA. In another embodiment, the isolated nucleic acid may comprise RNA. In an embodiment, the nucleic acid may comprise double-stranded DNA. Alternatively, the isolated nucleic acid may comprise single-stranded DNA. In an embodiment, the nucleic acid may comprise single-stranded RNA. Alternatively, the nucleic acid may comprise a double-stranded RNA or an RNA molecule comprising a double-stranded region. In yet another embodiment, the nucleic acid may comprise a RNA-DNA hybrid.

For example, in an embodiment, the isolated nucleic acid may comprise a genomic DNA sequence. The genomic DNA may be full-length, or may correspond to a partial gene sequence. In another embodiment, the isolated nucleic acid sequences may comprise a full-length or partial cDNA sequence. In another embodiment, the isolated DNA may comprise a short oligonucleotide.

In yet another embodiment, the isolated nucleic acid may comprise a RNA sequence. The RNA may comprise a full-length mRNA. Alternatively, the RNA may comprise a small inhibitory RNA which may be used to inhibit gene expression.

In an embodiment, the number of groups identified using the methods and systems of the present invention is correlated to the pattern of gene expression. In an embodiment, the plurality of data points comprise an array of DNA sequences hybridized to mRNA. The array of DNA sequences may comprise a solid-state array. For example, the data may comprise an array of DNA sequences of known identity hybridized to mRNA isolated from cells that are treated with a pharmaceutical agent over a period of time. Isolation of mRNA from the cells at various time points, and hybridization of the mRNA to the DNA array, can identify genes that may have changed expression profiles in response to the pharmaceutical agent. The present invention provides statistical tools for analyzing the thousands of data points that may result from such an experiment.

Thus, in an embodiment, the plurality of measured signals comprise hybridization data for a plurality of known gene sequences. Also, in an embodiment, the number of independent clusters identified by iterative ICA is correlated to the pattern of gene expression for the at least one cell type.

As described herein, the methods, products, and systems of the present invention provide for the development of mathematical models to explain gene expression profiles and how the expression of one gene may relate to the expression of a second gene. In an embodiment, the methods, products and software of the present invention correlate at least one of the measured signals, x, to the underlying source(s), s, generating the signal, and experimental noise, n. In an embodiment, the methods, products and software of the present invention correlate at least one of the measured signals, x, to the underlying sources, s, generating the signal, and experimental noise, n, as a function of time, t, such that: $x(t)=f(s(t))+n(t)$.

As described herein, the present invention recognizes that iterative ICA is uniquely suited to the analysis and grouping of gene expression data. In an embodiment, the iterative ICA used in the methods, products and systems of the present invention comprises an algorithm that yields three matrices that may be used to explain the interrelation between the genes whose expression is being monitored: (i) a set of basis functions $(s_1(t), s_2(t) \ldots s_M(t),)$ for each of the genes under study; (ii) a mixing matrix (A), and (iii) a separating matrix (W), wherein W is the inverse of A.

In an embodiment, raw data may be suitable for the algorithms of the invention. In some cases, however, it may be preferred to transform the data in some manner. For example, in an embodiment, the data may be transformed to describe the logarithm of the ratio of two signals, $y_i(t)=\log_2(R_i(t)/G_i(t))$, where R and G represent the measured signal for gene i measured under two different experimental conditions, over time, t. In an embodiment, R may correspond to gene expression for control cells and G may correspond to gene expression for experimental cells.

In an embodiment, the plurality of measured signals correspond to hybridization data used to measure the expression of a gene or a plurality of genes. For example, in an embodiment, the plurality of measured signals comprise a plurality of known DNA sequences hybridized to mRNA isolated from the at least one cell type. In an embodiment, the plurality of known DNA sequences are arranged to form a solid-state array. For example, microarrays such as those commercially available from AFFYMETRIX® (Santa Clara, Calif.) may be used.

The method provides the statistical tools to analyze the large number of data points generated in gene expression array hybridization experiments. In an embodiment, the number of data points analyzed using the methods, software products, and systems of the present invention is greater than 100 per single analysis. In other embodiments, the number of data points may be greater than 1,000 per single analysis, or greater than 10,000 data points per single analysis.

The computer-implemented methods, products, and systems of the present invention utilize an iterative ICA to describe an optimal number of independent gene groups that explain the gene expression profiles being measured. In an embodiment, the number of gene groups, n, is estimated as a preset number, $n_0$. The data may then be evaluated by increasing the number of groups from $n_0$ and performing an iterative analysis of the relative fit of the data using $n_0$ as compared to the new value of n. In an embodiment, the number of groups are increased incrementally by 1 group for each evaluation, such that the number of groups increases at each step from $n_0$, to $n_0+1$, to $n_0+2$, until the optimum number of groups $(n_{opt})$ is determined.

The method is designed such that the fit of the data to a certain number of independent gene groups may be evaluated during the course of the analysis, thus identifying the number of independent gene groups that best explains the data. The evaluation of the fit of the data to the current number, n, of independent gene groups may be performed at each iteration, or after several iterations (e.g., after 3 successive iterations, or the like). Also, in an embodiment, the method may comprise dynamic ICA such that the resulting model at least in part describes how the system changes over time.

In an embodiment, evaluation of the data fit includes the step of maximizing the mutual information within each of the resulting clusters or independent gene groups. Also, the evaluation of the data fit may comprise minimizing the mutual information outside of the resulting clusters or independent gene groups. Also, the evaluation of the data fit may comprise maximizing the information distance across clusters or hyper-volume outside of the resulting clusters or gene groups. The evaluation of the fit of the data to certain number of independent clusters may also comprise minimizing the information distance or hyper-volume within each of the resulting clusters or gene groups. As yet another level of analysis, the method may comprise using an independent method to analyzing the identified independent components for biological relevance. For example, in an embodiment, the expression profiles for known genes may be evaluated to determine if they are relevant to the biological function under study.

example, in an embodiment, the expression profiles for known genes may be evaluated to determine if they are relevant to the biological function under study.

In an embodiment, the ICA algorithm is designed to extract main signal trends to reduce or minimize computational memory required for matrix analysis. For example, the analysis may comprise hierarchical ICA such that the complexity of the computational analysis is reduced as the analysis proceeds by removing data inputs that have been described at earlier stages of the analysis from the set of data points still remaining to be characterized. Also, several commercially available ICA algorithms known to provide efficient analysis, with significantly reduced memory demands may be used. In an embodiment, the ICA algorithm is FastICA, which runs on MATLAB® software (The MathWorks, Inc., Natick Mass.) may be used. In an embodiment, efficient ICA algorithms may not be as accurate as standard ICA algorithms. Thus, an assessment of the ability of the algorithm to provide the analysis required may be performed using test data prior to utilizing a particular algorithm for the analysis or part of the analysis.

As with most statistical packages, the present invention may comprise removing signal due to noise from the data. Noise may be removed by a variety of methods known in the art including, but not limited to, filtering signals that are less than a pre-determined level. In another embodiment, removing noise may comprise the step of normalizing the variance of the data. For example, in an embodiment, normalization around the mean, median, start point, or end point may be performed.

In an embodiment, the present invention further allows for determining the dynamic interaction of genes within a gene group. In this way, the interrelationship of individual genes within a particular group of genes is described. In an embodiment, the cross-correlation between genes within a group is determined, wherein a positive cross-correlation comprises the situation in which the expression of one gene in the group is statistically correlated with the expression of a second gene in the same group. In an embodiment, the expression of one of the genes is dependent upon expression of the other gene. For example, the analysis may describe which genes are activated in response to a particular environmental stimulus or pharmaceutical agent. Additionally, the analysis may describe how the expression of one gene in the group affects, or is effected by, the expression of a second gene in the group, or a second gene in a different group.

In an embodiment, the relationship between genes within a group or in different groups is expressed as a mathematical model describing relative levels of gene expression for at least two of the genes in one or more groups. It is understood that gene expression does not occur in isolation and thus, may be influenced by, or reflect the contribution of, a variety of extraneous factors. For example, in an embodiment, the mathematical model that describes expression of genes $y_1, y_2 \ldots y_N$, in a group may include the contribution of at least one environmental factor. Or, the model may include the contribution of time. The model may also include the contribution of noise. For example, in an embodiment, the model comprises the expression $y_i = f(y_1, y_2, \ldots y_N, u_1, \ldots u_M) + e$, where $y_1, y_2 \ldots y_N$, is the expression of genes $1, 2, \ldots N$; $u_1, u_2 \ldots u_M$, corresponds to environmental factors $1, 2 \ldots M$, experimental noise is defined by e, and f is a linear or a non-linear function.

In some cases the mathematical model may be simplified such that the underlying physiological process is better revealed. For example, in an embodiment, contributions of extraneous factors and/or noise may be approximated using a simple function. Also in an embodiment, statistically weak links may be removed from the model. Finally, the model may be evaluated in light of test data to determine whether particular pathways are required to understand the phenomenon of interest.

The present invention further comprises systems using the computer-readable medium comprising iterative independent component analysis for gene expression array analysis. Thus, as described above, the present invention comprises a system for analyzing gene expression comprising using iterative independent component analysis (ICA) to identify an optimum number of independent clusters into which data comprising a plurality of measured signals may be grouped. In an embodiment, the system programming code for analyzing gene expression applies iterative independent component analysis (ICA) to data comprising a plurality of measured signals to identify an optimum number of independent clusters into which the data may be grouped.

The system may comprise an imaging unit as well as a means for the user to interact with the system as the analysis proceeds. Thus, in an embodiment, the present invention further comprises a unit for collecting and/or compiling data from said plurality of measured signals and transmitting said data to said computer, and a unit for transmitting the results of said analysis to a user.

In an embodiment, the systems of the present invention are designed for high-throughput analysis of DNA hybridization data. Thus, in an embodiment, the plurality of measured signals comprise a plurality of known DNA sequences hybridized to mRNA isolated from at least one cell type.

As described above, in an embodiment, the system utilizes an iterative ICA to provide an optimal number of independent gene groups that explain the gene expression profiles being measured. In an embodiment, the number of gene groups, n, is estimated as a preset number, $n_0$. The data may then be evaluated by increasing the number of groups from $n_0$ and performing an iterative analysis of the relative fit of the data using $n_0$ as compared to the new value of n. In an embodiment, the number of groups are increased incrementally by 1 group for each evaluation, such that the number of groups increases at each step from $n_0$, to $n_0+1$, to $n_0+2$, until the optimum number of groups ($n_{opt}$) is determined. Also, in an embodiment, the system comprises hierarchical ICA such that the complexity of the computational analysis is reduced as the analysis proceeds, by removing inputs that have been described at earlier stages of the analysis from the set of data points still remaining to be characterized. The system may also comprise determining if there is a cross-correlation between at least two data signals within a cluster group, wherein a positive cross-correlation comprises the situation in which the expression of one gene in the group is statistically correlated with the expression of a second gene in the same group. In an embodiment, expression of one of the genes may be dependent upon expression of the other gene.

DEFINITIONS

As used herein, the following terms shall have the definitions set out below.

In accordance with the present invention, conventional molecular biology, microbiology, and recombinant DNA techniques may be used that will be apparent to those skilled in the relevant art. Such techniques are explained fully in the literature (see, e.g., Maniatis, Fritsch & Sambrook, "Molecular Cloning: A Laboratory Manual (1982); "DNA Cloning: A Practical Approach," Volumes I and II (D. N. Glover ed. 1985).

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes.

DNA molecules may be identified by their nucleic acid sequences, which are generally presented in the 5' to 3' direction (as the coding strand), wherein 5' and 3' indicate the linkages formed between the 5'-hydroxy group of one nucleotide and the 3'-hydroxyl group of the next. For a coding-strand sequence presented in the 5'-3' direction, its complement (or non-coding strand) is the DNA strand which hybridizes to that sequence.

The term "gene" means a region of DNA encoding for the mRNA sequence that codes for a given protein/polypeptide along with elements regulating mRNA expression.

"Messenger RNA" or "mRNA" shall mean an RNA molecule that encodes for a polypeptide.

"Complementary DNA" or "cDNA" shall mean the DNA molecule synthesized by polymerization of deoxyribonucleotides from an RNA template by an enzyme with reverse transcriptase activity.

An "isolated nucleic acid" is a nucleic acid the structure of which is not identical to that of any naturally occurring nucleic acid or to that of any fragment of a naturally occurring genomic nucleic acid spanning more than three separate genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein.

"Oligonucleotide", as used herein, is defined as a molecule comprised of two or more deoxy- or ribonucleotides, preferably more than eight. Its exact size will depend upon many factors which, in turn, depend upon the ultimate function and use of the oligonucleotide.

A "DNA fragment" includes polynucleotides and/or oligonucleotides and refers to a plurality of joined nucleotide units formed from naturally-occurring bases and cyclofuranosyl groups joined by native phosphodiester bonds. This term effectively refers to naturally-occurring species or synthetic species formed from naturally-occurring subunits. "DNA fragment" also refers to purine and pyrimidine groups and moieties which function similarly but which have non naturally-occurring portions. Thus, DNA fragments may have altered sugar moieties or inter-sugar linkages. Exemplary among these are the phosphorothioate and other sulfur containing species. They may also contain altered base units or other modifications, provided that biological activity is retained. DNA fragments may also include species that include at least some modified base forms. Thus, purines and pyrimidines other than those normally found in nature may be so employed. Similarly, modifications on the cyclofuranose portions of the nucleotide subunits may also occur as long as biological function is not eliminated by such modifications.

As used herein, the term "hybridization" refers generally to a technique wherein denatured RNA or DNA is combined with complementary nucleic acid sequence that is either free in solution or bound to a solid phase. As recognized by one skilled in the art, complete complementarity between the two nucleic acid sequences is not a pre-requisite for hybridization to occur. The technique is ubiquitous in molecular genetics and its use centers around the identification of particular DNA or RNA sequences within complex mixtures of nucleic acids.

A polypeptide refers to any peptide generated from a protein or the full-length protein itself. A polypeptide may include the full-length protein or a fragment generated by proteolytic cleavage, chemical cleavage, or other means.

Independent component analysis (ICA) decomposes an input dataset into components so that each component is as statistically independent from the others as possible. ICA groups the data into groups or clusters such that the correlation for individuals within a group is maximized (i.e., intragroup samples are highly correlated), while the correlation for individuals in separate groups is minimized (i.e., samples in different groups show minimal correlation).

Iterative independent component analysis performs ICA in an iterative manner such that the analysis is performed for a successively increasing number of independent groups or clusters until the fit of the data starts to decrease. At the point where the fit of the data ceases to improve, the analysis considers the number of independent groups to be optimized.

As used herein, an array or microarray is a solid-state grid containing short sequences of nucleic acid (usually DNA) of known sequence fixed at a particular position (or address) on the grid. DNA arrays are usually termed microarrays due to the small size of the grid and the small amounts of nucleotide (e.g., $\mu M$ or nM amounts) present at each address.

Data fitting is a process in which a model is presented to fit all or most of the given data points.

Mutual information is an information theoretic measure that quantifies the amount of information shared by two random variables.

Information distance is an information theoretic measure that quantifies the amount of disparity and dissimilarities between the information provided by two random variables.

Hyper-volume is the multi-dimensional space occupied by a multi-dimensional variable or function.

Efficient ICA, as used herein, is a version of ICA that while maintaining the given n−1 independent components, analyzes the signals to produce the nth independent component.

Normalized data, as used here, refers to a process in which signals are standardized by removing their mean (or median) and dividing by their standard deviation (or quartile).

Variance is a measure of scattering of the data points defined based on the second order distance of the points from the mean.

As used herein, cross-correlation is understood as a dependency of expression of one gene in the group upon the expression of a second gene in the group. Thus, a positive cross-correlation comprises the situation in which the expression of one gene in the group is statistically correlated with the expression of a second gene in the same group such that the expression of one of the genes is dependent upon expression of the other gene.

As used herein, a computer program comprises a computer-encoded language that encodes the steps required for the computer to perform a specific task or tasks.

Also, as used herein, software comprises the computer program(s) used in conjunction with any other operating systems required for computer function.

As used herein, the singular forms "a", "an" and "the" include plural references unless the context clearly dictates otherwise.

Gene Array Analysis Techniques

DNA microarrays are essentially solid-state grids containing short sequences of DNA of known sequence fixed at a particular position (or address) on the grid (Bassett, D. E., et al., *Nature Genetics*, 21:51-55, 1999; Hughes T. R., et al., *Curr. Opin. Chem. Biol., February;* 5:21-5, 2001; Harkin D. P., *Oncologist*, 5:501-7, 2000; Southern, E., et al., *Nature Genetics*, 21: 5-9, 1999; Greenberg S. A., *Neurology*, 57:755-61, 2001; Schulze A., *Nat. Cell. Biol., August;* 3(8):E190-5, 2001; Bowtell, D. D., *Nature Genetics*, 21:25-32, 1999; Devaux, F., et al., *FEBS. Lett.*, 498:140-4, 2001; Cheung, V. G., et al., *Nature Genetics*, 21:15-19, 1999; Blohm, D. H., et al., *Curr. Opin. Biotechnol.*, 12:41-7, 2001; Hegde P., et al., *Biotechniques*, September; 29(3):548-50, 2000, Duggan, D. J., et al., *Nature Genetics*, 21:10-14, 1999, Hacia, J. G., *Nature Genetics*, 21:42-47, 1999. In some cases, the DNA sequences are short fragments of DNA generated from a library. Alternatively, some arrays comprise oligonucleotide sequences (short fragments of DNA less than 50 nucleotides long) each of which may only differ by one base pair (commercially available from AFFYMETRIX®, Santa Clara, Calif.).

Regardless of how the array is formulated, DNA microarrays may be used to identify genes expressed in the cell. When mRNA isolated from a cell is hybridized to a DNA array, the DNA sequences complementary to the expressed mRNA will exhibit hybridization. The mRNA may be tagged (e.g., with a fluorescent label or a radiolabel) so that hybridization can be detected as a spot (or signal) at a particular address on the array. Once the address is determined, the DNA sequence complementary to the gene being expressed may be used to identify the mRNA product and thus, the gene encoding the mRNA.

To detect changes in gene expression, the cell may be perturbed, as for example, by adding a drug or changing the environmental conditions, and isolating mRNA from the perturbed cells. The mRNA may then be labeled (or tagged) as described above and hybridized to the array. By controlling the hybridization conditions, the signal generated by the tagged mRNA is proportional to the mRNA in the sample. Thus, the image of the microarray upon hybridization of the tagged mRNA will identify those genes that have changes in expression relative to the array probed with mRNA from a control cell. In many cases, it is the change over time which is of interest and so, a microarray will be analyzed by hybridizing the array to mRNA isolated at varying time points after or during perturbation of the cell of interest. With each array having thousands of unique DNA sequences each at a unique address, correlating gene expression measured as hybridization to one or several microarrays can be a daunting task.

Many techniques have been applied to the problem of making sense of large amounts of gene expression data. Cluster analysis techniques (e.g., K-Means), self-organizing maps (SOM), principal components analysis (PCA), and other analysis techniques are all widely available in packaged software used in correlating this type of gene expression data.

Cluster analysis is a loose term covering many different algorithms for grouping data. Clustering can be divided into two main types: top-down and bottom-up. Top-down clustering starts with a given number of clusters or classes and proceeds to partition the data into these classes. Bottom-up clustering starts by grouping data at the lowest level and builds larger groups by bringing the smaller groups together at the next highest level.

K-Means is an example of top-down clustering. K-means groups data into K number of best-fit clusters. Before using the algorithm, the user defines the number of clusters that are to be used to classify the data (K clusters). The algorithm randomly assigns centers to each cluster and then partitions the nearest data into clusters with those centers. The algorithm then iteratively finds new centers by averaging over the data in the cluster and reassigning data to new clusters as the centers change. The analysis iteratively continues until the centers no longer move (Sherlock, G., *Current Opinion in Immunology*, 12:201, 2000).

Tree clustering is an example of bottom-up clustering. Tree clustering joins data together by assigning nearest pairs as leaves on the tree. When all pairs have been assigned (often according to either information-theoretical criteria or regression methods), the algorithm progresses up to the next level joining the two nearest groups from the prior level as one group. Thus, the number and size of the clusters depends on the level. Often, the fewer clusters, the larger each cluster will be. The stoppage criteria for such algorithms varies, but often is determined by an analysis of the similarity of the members inside the cluster compared to the difference across the clusters.

Self-organizing maps (SOMs) are competitive neural networks that group input data into nearest neighbors (Torkkola, K., et al., *Information Sciences*, 139:79, 2001; Toronen, P., et al., *FEBS Letters*, 451:142-146, 1999). As data is presented to the neural network, neurons whose weights currently are capable of capturing that data (the winner neuron) are updated toward the input. Updating the weights, or training the neural net, shifts the recognition space of each neuron toward a center of similar data. SOMs are similar to K-means with the added constraint that all centers are on a 1 or 2 dimensional manifold (i.e., the feature space is mapped into a 1 or 2 dimensional array, where new neighborhoods are formed). In SOM, the number of neurons is chosen to be much larger than the possible number of the clusters. It is hoped that the clusters of trained neurons will provide a good estimation of the number of the neurons. In many cases, however, a number of small clusters are formed around the larger clusters, and there is no practical way of distinguishing such smaller clusters from, or of merging them into, the larger clusters. In addition, there is no guarantee that the resulting clusters of genes actually exhibit statistically independent expression profiles. Thus, the members of two different clusters may exhibit similar patterns of gene expression.

Principal component analysis (PCA), although not a clustering technique in its nature (Jolliffe, I. T., Principal Component Analysis, New York: Springer-Verlag, 1986) can also be used for clustering (Yeung, K. Y., et al., *Bioinformatics*, 17:763, 2001). PCA is a stepwise analysis that attempts to create a new component axis at each step that contains most of the variation seen for the data. Thus, the first component explains the first most important basis for the variation in the data, the second component explains the second most important basis for the variation in the data, the third component the third most important basis, and so on. PCA projects the data into a new space spanned by the principal components. Each successive principal component is selected to be orthogonal to the previous ones, and to capture the maximum information that is not already present in the previous components. The principal components are therefore linear combinations (or eigenarrays) of the original data. These principal components are the classes of data in the new coordinate generated by PCA. If the data is highly non-correlated, then the number of significant principal components can be as high as the number of original data values. If, as in the case of DNA microarray experiments, the data is expected to correlate among groups, than the data should be described by a set of components which is fewer than the full complement of data points. PCA is a highly efficient dimension-reduction technique. One of the disadvantages of PCA, however, is that the resulting coordinates often have no physical meaning. Thus, it is often not possible to extract rules and patterns from the resulting clusters. Another disadvantage is that PCA assumes that the clusters are orthogonal (perpendicular) to each other; in reality, this is often not the case.

In many cases, these techniques cannot accurately describe the true number of gene groups. For array analysis, the analysis may provide vastly different results depending upon how many independent gene groups are assumed. Thus, inaccurate clustering analysis can skew the data such that results of further analyses are compromised.

Another disadvantage of the existing microarray processing technologies is the lack of a reliable method for eliminating signals due to noise. Microarray measurements are hybridization-based and thus, the location and/or intensity of a signal may vary with experimental conditions. Also, some genes have high variance in their expression profiles. In some cases, genes with noisy expression profiles unrelated to the physiological process under study can complicate the clustering techniques and result in too many clusters. Finally, noise may result from the misidentification of samples or other human error.

ICA for Cluster Analysis

The present invention is distinct from previous microarray analysis techniques in that it employs iterative independent component analysis (iterative ICA) as a means to determine the optimal number of independent gene groups (i.e., clusters) that best explains the data. Although computationally intensive, ICA is particularly suited for cluster analysis. ICA decomposes an input dataset into components so that each component is as statistically independent from the others as possible. Thus, in ICA, data is clustered such that the correlation for individuals within a group is maximized (i.e., intra-group samples are highly correlated), while the correlation for individuals in separate groups is minimized (i.e., samples in different groups show minimal correlation).

ICA is commonly applied to blind source separation (BSS). An example of BSS often used portray ICA is the cocktail party problem. At a cocktail party, an individual in one group has to be able to concentrate on one set of audio signals amongst the din of audio signals from several other groups. Assuming that each group is talking about issues that are unrelated to each other, an individual in the first group is usually capable of following the conversation in their own group and separating that conversation from those of other groups. The blind separation of a rather small number of signals from independent sources may be a rather easy task for the human brain, but it is an extremely difficult task for a computer—especially when the number of interfering signals is very large. ICA has been used for discerning underlying patterns in a set of signals, such as electroencephalographic (EEG) signals (Makeig, S., et al., *Proceeding of the Advances in Neural Information Processing Systems*, Eds., Touretzky et al., MIT Press, pp. 145-151, 1996; Vigario, R., et al., *Electroenceph. Clin. Neurophysiol.*, 103:395-404, 1997), magnetic resonance imaging (MRI) signals (Stone, J. V. et al., *NeuroImage*, 15:407-421, 2002), and even financial data (Back, A. D., et al., *Int. J. Neural Syst.*, 8:473-484, 1997).

In the microarray problem, the true objective is to identify groups of genes that that are activated and/or suppressed in response to certain biological changes or signals. Unlike PCA, ICA can take higher order statistics into account, and can utilize non-orthogonal transformation. The present invention recognizes that because ICA is capable of identifying groups of entities with highly similar statistical characteristics, ICA is highly suitable for microarray processing. Once the independent groups of genes are identified, the correlation, and in some cases the causality, of gene expression among these gene groups can be explored more effectively.

ICA has recently been applied to microarray analysis. For example, it has been shown that as compared to PCA, ICA can be superior in clustering yeast genes in such a manner as to mirror known expression profiles (Hori, G., et al., Blind gene classification on ICA of microarray data, ICA 2001 meeting, SanDiego, U.S.A., pp. 332-336). Also, Lee and Batzogou (Lee, S.-I. et al., *Genome Biology*, 4:R76, October 2003) describe the use of ICA to fit microarray data to a predetermined number of gene expression groups. Both of these studies, however, pre-specified the number of clusters (i.e., gene groups) into which the data should be fit. In contrast, the method of the present invention does not require a pre-specified number of clusters but finds the optimal number of clusters automatically. Also, and as described herein, the method of the present invention has the ability to incorporate the dynamics and convolution of signals in time into the analysis.

The fundamental equation for ICA is as follows.

$$x(t)=f(s(t))+n(t) \quad (1)$$

In an embodiment, $s(t)=(s_1(t), s_2(t), \ldots s_M(t))^T$, represents the underlying sources, $n(t)=(n_1(t), n_2(t), \ldots n_M(t))^T$, represents the noise in the system, $x(t)$ represents the experimentally measured signals, "T" defines the transpose operation, and f is a function that mixes the sources. From this fundamental equation many specialized techniques have been developed. For example, a linear mixing model would replace equation (1) with equation (2)

$$x(t)=As(t)+n(t) \quad (2)$$

where A is the mixing matrix.

Classical ICA is a linear mixing model that ignores the noise term and gives the simple relation shown in equation (3).

$$x(t)=As(t) \quad (3)$$

In an embodiment, the method employs linear ICA. In linear, ICA, determination of the relationship between the expression of genes and/or gene clusters and the biological processes requires estimation of, W, the inverse of the matrix A (i.e., $W=A^{-1}$) to reconstruct s from x. The goal of ICA is to estimate W (de-mixing matrix) to thereby estimate the sources, s, from the measured expression levels, x. This may be done using static ICA (e.g., Lee and Batzoglou, 2003) or other types of ICA.

For example, the equation used to iteratively estimate W(new) (the next updated value of matrix W) based on W(old) (the present value of matrix W) is:

$$W(\text{new}) = W(\text{old}) - \frac{[E\{xg(W(\text{old})^T x)\} - \alpha W(\text{old})]}{[E\{g'(W(\text{old})^T x)\} - \alpha]} \quad (4)$$

where: $E[.]$ represents a statistical expectation function, $\alpha$ is a parameter controlling the rate of convergence, and $g(.)$ is a sigmoid function. For example, in an embodiment, a choice of sigmoid function g is:

$$g(r) = \tan h(cr) \quad (5)$$

where c is a constant, and r is the variable. Other sigmoid functions such as $\tan^{-1}(.)$, may also be used.

There are many other versions of ICA, however, that are each specialized for a particular functionality and that may be used with the methods of the present invention. For example, ICA may be used to model a cell having M independent biological processes forming an M-dimensional time-series, s(t). For example, a set of biological processes of interest may be monitored by microarray analysis as the time variation in gene expression of N genes where the interaction among M biological processes and the expression of N genes may be represented as an N-dimensional microarray expression time-series x(t). In this way, the system may be analyzed using ICA that attempts to recover unknown s(t) from measured x(t).

For example, it may be assumed that $y_i(t)$ is the gene expression of gene i through time steps t=1, 2, ..., K, where K is the number of time steps. Now, assume that N is the number of genes passing through the filtering stage, P is the degree of the dynamics the system (i.e., the maximum delay in time for which the previous expressions can still affect the expression levels in the present time). One may define the time-dependent matrix x(t) as follows.

$$x(t) = \begin{bmatrix} y_1(t) \\ y_1(t-1) \\ y_1(t-2) \\ \vdots \\ y_1(t-P) \\ y_2(t) \\ y_2(t-1) \\ \vdots \\ y_2(t-P) \\ \vdots \\ y_N(t) \\ y_N(t-1) \\ \vdots \\ y_N(t-P) \end{bmatrix} \quad (6)$$

As can be seen, x(t) has all gene expression signals and the delayed version of these signals in it. The present invention, unlike methods utilized previously, has the ability to identify the sources s(t) that can generate such a dynamic system.

As discussed above, conventional ICA requires that the number of clusters be pre-specified. As with other analysis techniques, choosing an unrealistic number of clusters can result in groups that are too small and unevenly scattered, or too large with unacceptably large inter-cluster variation. In addition, when an unsuitable estimation of the number of clusters is used, correlating the resulting non-optimal clusters with the physiological or biological changes can be very challenging, because many of the resulting clusters do not have truly significant biological significance.

In contrast to previous applications of ICA to gene expression data, the present invention determines the optimal number of "clusters" or gene groups into which the data best fits. A general block diagram of the method of the present invention is shown in FIG. 1. First, mRNA is isolated from an individual or a cell type of interest. For example, in an embodiment, mRNA may be harvested from cells (80) before (A) and after (B) treatment of the cells with a drug. The mRNA can then be labeled in some manner, as for example with a fluorescent tag, and hybridized to an array (or microarray) of DNA fragments (90). Generally, the array of DNA fragments comprises individual DNA fragments of known sequence at each array address. Thus, the DNA at address 1 may comprise sequence a, the DNA at address 2 may comprise sequence b, and so on. Under the proper experimental conditions, the mRNA that has a sequence complementary to the DNA fragment at a particular address will hybridize to the DNA at that address, but not to DNA fragments at other addresses. In this way, a pattern of hybridization signals, comprising mRNA bound to the array is generated (100). As is known in the art, the hybridization pattern generated will depend on the mRNA pool being hybridized to the array, as well as the experimental conditions used for hybridization. For example, the data may comprise expression levels correlated to a biological response, such as bone healing.

In an embodiment, hybridization of the array to (A) mRNA and (B) mRNA may be done as a separate hybridizations. Alternatively, the hybridization may be performed such that mRNA (A) is labeled with a green fluorophore and mRNA (B) is labeled with a red fluorophore. In this way, hybridization for the two mRNA pools is conducted under identical conditions and imaging software may be used to quantitatively distinguish the signals.

ICA of array hybridization data may utilize either the raw data (i.e., in linear scale) or may apply the data transformed in some manner (120). For example, the analysis may employ log scaled data in form of $y_i(t) = \log_2(R_i(t)/G_i(t))$, where R and G represent two different profiles of gene expression measured using red and green fluorophores. For example, as described above, in addition to the experimental samples labeled with a red fluorophore, a control (e.g., prior to fracture) labeled with a green fluorophore is included. Thus, the multi-dimensional time-series y(t) will represent the log ratios of experimental (red) and green (reference) intensities at time, t. Also, in many cases non-linear functions may be used to describe gene expression, as for example where expression includes multiplicative effects from enzyme cascades, lags in causality, or oscillatory behavior (e.g., Lee and Batzogou, 2003).

A variety of systems known in the art may be used for image analysis (110) and compiling the data (120). For example, where the mRNA is labeled with a fluorescent tag, an fluorescence imaging system (such as the microarray processor commercially available from AFFYMETRIX®, Santa Clara, Calif.) may be used to capture, and quantify the extent of hybridization at each address. Or, in the case where the mRNA is radioactive, the array may be exposed to X-ray film and a photographic image made. Once the data is collected, it may be compiled to quantify the extent of hybridization at each address as for example, using software to convert the measured signal to a numerical value.

In an embodiment of the present invention, the first step of signal analysis after the imaging data has been collected (110) and collated and/or transformed into a quantitative signal (120), is to filter noise from the data (130). In an embodiment, filtering may be conducted via a thresholding mechanism in which genes whose expression levels are always less than the noise level for the microarray are removed from the pool. Alternatively, variance normalization techniques may be applied to the data. Such variance normalization may include, but is not limited to, statistical techniques on based on the normalization around mean, median, start point, or the endpoint. Software for performing data normalization as a means to remove noise from data sets includes, but is not limited to, MATLAB® (The MathWorks, Natick, Mass.) and SAS (SAS Institute, Inc., Cary, N.C.).

In an embodiment, an autocorrelation function and/or power spectra of the expression signals based on the Fourier Transform of the correlation function may be applied to remove noise from the data (131). In this approach, the autocorrelation of the time signal for each gene is calculated, and based on the smoothness of the autocorrelation function, as well as the power spectra, noise-like variation may be eliminated using predetermined statistical criteria. Autocorrelation is used to detect non-randomness in variables. Patterns having a spike-like autocorrelation function or a flat power spectra are most likely to be noise patterns and thus, may be filtered out.

Also, the method and systems may further comprise using an independent method to analyze the identified independent components for biological relevance. For example, the data may be compared to the known biological changes of interest to determine if outlying signals may be due to obvious experimental or human error, or created by another biological process that is not of interest in the conducted experiments (132). This allows the user to intelligently eliminate or reduce the chances of corrupting the results with noisy or non-relevant data. As an example, the gene variations due to stress are known to corrupt gene expression data in many experiments. If the pattern of gene expression associated with such environmental factors is known (e.g., the pattern of gene expression associated with heat-shock or other types of stress), the genes highly correlated with this factor can be identified and removed from the pool of genes to be investigated for other types (i.e., non-stress related) of biological interactions.

Finally, there may be an analysis whereby missing data is approximated (133). For this, in time-series, spline approximators may be used to estimate the missing data points if the neighboring points in the time series are known (Ziv Bar-Joseph, et al., *Proc. Natl. Acad. Sci., U.S.A.,* 100:10146-10151, 2003).

Still referring to FIG. 1, once the signals have been corrected for noise, they may be passed to the next step: iterative ICA determination of the number of gene groups (140). For iterative ICA, a small number $n=n_0$ (in many cases $n_0=2$) is chosen as the initial guess for the number of independent gene expression groups (141). With the assumption $n=n_0$ an ICA algorithm is performed on the data (142) and the fit of the data to the model is evaluated (143). The data then analyzed for an increasing number of independent groups until the fit of the data no longer improves (144). The number of independent gene groups providing the best fit is then chosen as the optimal number of independent components.

Thus, embodiments of the present invention comprise the use of iterative ICA to generate clusters that are independent and meaningful. Assuming that $n=n_0$ is a reasonable assumption (i.e., that the user has pre-selected the correct number of gene groups), the analysis is complete. In most cases, however, an analysis based on a pre-determined number (or initial estimate $n_0$) of gene groups is often far from reality and must be improved. For example, the assumptions made on the number of clusters are often based on the underlying biological factors, and may or may not be accurate. For biological studies where the number of gene groups can be guessed, $n_0$ is usually selected to be an integer slightly smaller than the estimated number. For the applications where biology cannot provide an estimation of the underlying gene groups, $n_0$ is set to number 2. Regardless of the suitability of the initial value of $n=n_0$, the algorithm of the present invention will search for the optimal number of the gene groups.

To optimize the number of clusters, the fit of the data with an increasing number of clusters may be quantitatively assessed. The number of clusters is sequentially increased (i.e., from $n_0$, to $n_0+1$, to $n_0+2$, ... to $n_0+i$) until the fit starts to decrease. At this point, the previous number of clusters is selected as optimal (e.g., $n_0+(i-1)$).

At least four criteria may be used for cluster optimization: (1) maximizing the mutual information (i.e., correlation) within each of the resulting groups (146) (compared to the previous values of n); (2) minimizing the mutual information between (outside of) groups (147) (compared to the previous values of n); (3) minimizing the information distance (i.e., hyper-volume) within each of the resulting groups (146) (compared to the previous values of n); and (4) maximizing the information distance (i.e., hyper-volume) between each of the resulting groups (147) (compared to the previous values of n). Additionally, in yet a further embodiment, the groups are evaluated to be sure that each group has a unique pattern (i.e., no two groups describe the same expression profile) (148).

Thus, for the first iteration when $n=n_0$, it is always assumed that the condition is non-optimal and therefore, the new value of n is set as $n=n+1$. In subsequent iterations, the criteria described above are tested and if the condition is not yet optimal, n is incremented. At some point, however, it is determined that a condition is in fact optimal (i.e., a minimal intra-group variance and maximal inter-group variance), such that any further increase in the number of clusters reduces the fit. At this point, clusters obtained with the previous value of n are chosen to be optimal and are sent to the next step. In an embodiment, the number of clusters defined accurately approximates the number of gene groups, or independent biological processes(s).

In an embodiment, the results of the dynamic ICA algorithm yield three matrices. The first matrix defined by ICA contains a set of basis functions (i.e., s(t) in formulas above). The second matrix contains the mixing matrix (i.e., A in the formulas above), and the third matrix contains the separating matrix (W).

There are many types of ICA algorithms that may be used for the analysis techniques of the present invention. For example, linear ICA algorithms may be employed. Linear algorithms may be preferred for the analysis of large data sets of microarray data. Also, non-linear ICA algorithms (such as P. Pajunen, A. Hyvärinen and J. Karhunen "Non-Linear Blind Source Separation by Self-Organizing Maps" *Proc. Int. Conf. on Neural Information Processing*, Hong Kong, pp. 1207-1210, 1996) may also be employed. Non-linear algorithms may be better suited to data sets comprising fewer gene groups due to the ability of these algorithms to analyze non-linearly combined signals.

There are, however, certain disadvantages associated with existing ICA techniques. First, ICA is computationally intensive when applied to a large number of inputs assuming different number of independent components. Thus, if ICA is to be performed iteratively, the recursive process on a large set of inputs can be computationally time-consuming. In addition, traditional ICA algorithms do not provide information about the dynamics and time convolutions of the signals.

Thus, traditional ICA methods are "static" nature, in that the information provided for one point in time is not correlated to information at other points in time.

Thus, in an embodiment, the ICA algorithm may comprise a means to reduce the computational intensity required for each step. For example, an ICA algorithm called FastICA (available from the Helsinki University of Technology, Laboratory of Computer and Information Science) may be implemented in MATLAB® 6.0 (The MathWorks, Inc., Natick, Mass.) using a 1 GHz AMD ATHLON PROCESSOR®. Although not as accurate as the original ICA, FastICA provides a much faster technique when large datasets are used.

Also, in an embodiment, the algorithm has a hierarchical structure that reduces the computational complexity of the ICA algorithm. When performing hierarchical ICA, after a new independent component is generated, the inputs that have been estimated by the linear/non-linear combination of the existing independent components (based on the mixing matrix) may be removed from the pool of inputs. In this way, at each step, some of the signals (i.e., genes) are removed from the pool and ICA is performed on a smaller number of remaining genes in the next step. Thus, the number of inputs after the generation of the first few components is significantly reduced, thereby making the iterative process much faster. Hierarchical ICA reduces the computational complexity of the calculations exponentially as the analysis proceeds. Also, hierarchical ICA provides a more accurate clustering technique in that the threshold values for each cluster may be adaptively tuned throughout the analysis. This adaptive tuning can avoid generation of overly large clusters with poorly correlated samples. Such tuning has been shown to reduce the generation of overly small and condensed clusters.

Also, in an embodiment, a type of dynamic ICA is used for the analysis. Attributes of dynamic ICA algorithms which make these algorithms particularly suited for array analysis include improved matrix utilization and the inclusion of the dynamics of variations of the measured effect over time. An application of such a method would be quantitative dynamic modeling and analysis of the effect of a drug on genetic pathways involved in a disease throughout the course of treatment. Standard (non-dynamic) ICA algorithms provide for the separation of signals but do not adjust the analysis to explain with the effect of the convolution of signals in time.

Figure 2:
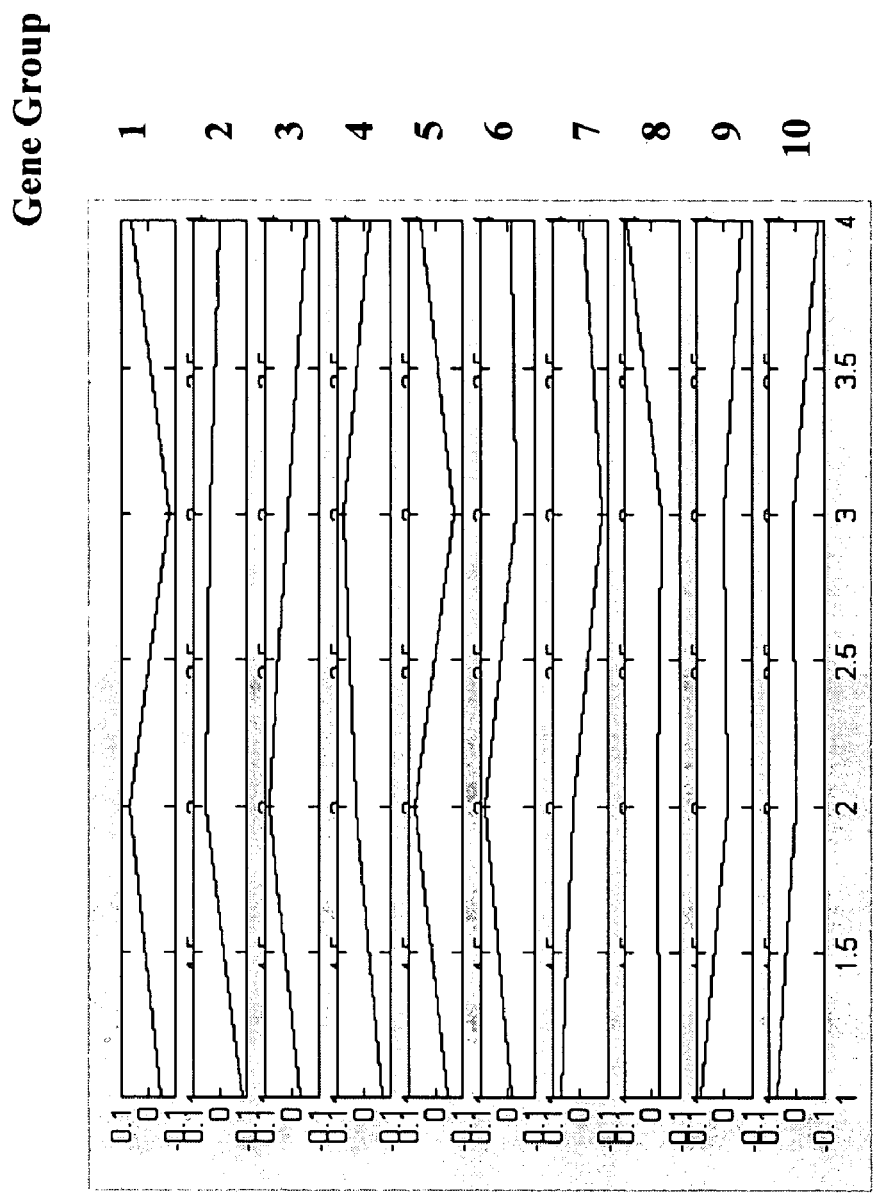
FIG. 2 shows ten separate independent gene clusters identified for an array experiment measuring relative gene expression for rats during the bone fracture healing process in accordance with an embodiment of the present invention.

FIG. 2 shows an example of the application of the iterative ICA of the present invention to the analysis of gene expression relating to bone healing. Thus, in an embodiment, the signals are processed to remove noise by subtracting the means from each data point and the ICA signal components, s(t) are plotted. In FIG. 2, the vertical axis is the amplitude of the signal and the horizontal axis shows time in hours. In an embodiment, each of the independent components (1-10) shows a different expression profile. The independent components are themselves linear combinations of the original gene expression data. As such, they best represent separate "pathways" of expression or groups of related genes. In other words, each gene group may be understood as representing independent sets of genes that have patterns of gene expression that are somehow correlated to each other.

Once the genes have been clustered into separate groups, the next task is to determine what genes are included in the group. Hybridization based assays are designed to measure the relative levels of signal present at each address. Thus, in some cases, there may be a background signal even for genes that are not being expressed by the cell type being assayed. Because of the high levels of background or other types of noise prevalent in these types of experiments, in many cases, a linear combination of the original input does not yield a simple zero contribution for genes not used on the pathway. Thus, in an embodiment, a decision must be made about what cutoff is useful for choosing a gene's contribution to the pathway.

As an example, for the first independent component shown in FIG. 2 (i.e., gene group 1), the maximum mixing coefficient in matrix A is over 2,000 and the minimum mixing coefficient is under −2,100. The entries in matrix A are dimensionless and therefore, have no units. The number of genes identified as being part of the group may in part depend on the cutoff value used. For example, if values within a range comprising less than 20% of the maximum or more than 20% of the minimum are chosen, the number of contributing genes for the first gene group (Gene group 1 in FIG. 2) is 750. Choosing a cutoff value of 5% reduces the number of genes in the group to 94. Thus, in an embodiment, the cut-off values are designed to eliminate the chances of creating too large or too small groups.

Figure 3:
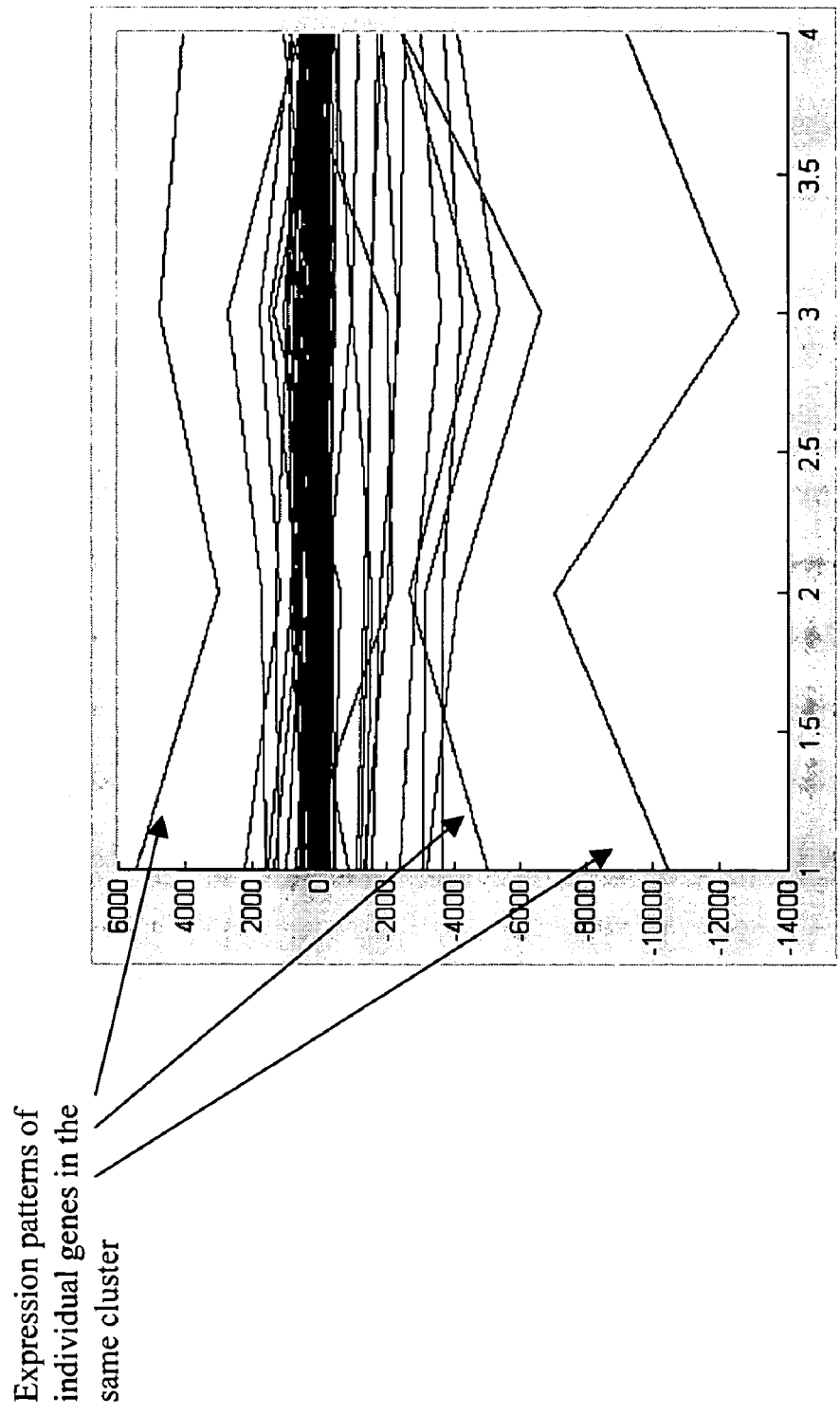
FIG. 3 shows relative expression as a function of time as derived for the 94 expressed genes in the first independent component (i.e., gene cluster) of FIG. 2 (Gene group 1) in accordance with an embodiment of the present invention.

FIG. 3 shows a composite of all 94 signals for the genes in Group 1 of FIG. 2. Although the figure is highly compressed in some regions, some of the outer sequences can be seen to have highly correlated expression profiles.

Application of iterative ICA to the analysis of gene expression data can identify genes that are correlated in both the same sense as well as in the opposite sense for the same biological process of interest. Genes that are correlated in the same sense are genes whose relative levels of expression react in the same manner to a given stimulus. Genes that are correlated in the opposite sense are genes whose relative levels of expression react in an opposite manner to a given stimulus. For example, the stimulus of a change in temperature may be associated with an increase in expression for genes A and B and an inhibition of expression for gene C. In this case, genes A and B are correlated in the same sense with each other, but in an opposite sense with gene C. For example, in FIG. 3, it can be seen that whereas some genes have almost identical profiles (at least qualitatively), other gene profiles are almost mirror images to each other.

Iterative ICA can also identify genes that have a delayed response as compared to other genes in the group. For example, in some cases, gene E is activated in response to activation of gene D. Thus, activation of gene E may be delayed relative to gene D. Signals for genes that have a delayed response to other genes may appear to be shifted as compared to the triggering gene (e.g., gene D) when gene expression is analyzed as a function of time.

Correlation of Gene Groups To a Biological Response and Defining the Interrelationship Between Genes in a Group In the next step, gene groups identified by ICA may be matched to particular biological response pathway (150) (FIG. 1). For example, as described above, it may be determined that genes in group 1 display a profile similar to known metabolic genes, whereas genes in group 2 are involved in cholesterol metabolism, genes in group 3 are involved in carcinogenesis, and genes in group 4 are involved in bone healing. Once genes have been matched to a specific biological process (151), the relationship among genes within a group may be defined (152) (FIG. 1).

A. Correlation of Group to Biological Response

To correlate a specific gene cluster to a biological pathway or response, the pattern of gene expression for each group may be compared to a signal that shows the observed biological events or changes. For example, the biological event(s) may be the amount of cartilage formation during the healing of bone.

Thus, the first step involves determining whether any of the clusters identified by ICA are correlated with, and therefore may be biologically relevant to, a particular physiological process. If signals representing the biological/physiological changes are available, the correlation among the measured signal(s) for each cluster as determined by iterative ICA can identify the clusters that are correlated with the biological or physiological response under study. In this way, a particular independent component, or gene group, is identified (or "stamped") as being involved in the physiological process or biochemical pathway of interest.

For example, it may be found that out of 10 independent components (e.g., gene groups 1-10 of FIG. 2) group 3 has patterns of gene expression that are correlated to the process of bone re-growth. Genes in group 3 would then be "stamped" as being involved the bone healing.

B. Modeling the Interaction Between Genes Within a Group

Once the clusters involved in a biological study are identified, the genes of the relevant clusters are placed into set for further analysis. Essentially, this set of genes comprises a pool of candidate genes that may be involved in mediation of the biological change of interest. For example, the biological change of interest may comprise bone re-growth and there may be five genes in the cluster identified as important for bone re-growth.

Next, a model may be applied to relate the expression levels of each of the genes in the cluster pool to each other. The model may be linear or nonlinear. Preferably, the model relates the expression level of all genes ($y_1, y_2, y_3, \ldots y_N$) to each other and to the environmental factors ($u_1, u_2, u_3, \ldots u_M$), such as concentration of a chemical, temperature, or other type of treatment. The model may also estimate the level of uncertainty inherent to the model by considering a noise factor (e) in the equations. Thus, the model may be shown as follows:

$$y_1 = f(y_1, y_2, \ldots, y_N, u_1, \ldots, u_M) + e \quad (7)$$

It can be seen that in its most general form, the model is a nonlinear. In many cases, however, a linear model provides a good fit to the data. This might be expected in the situation where the genes of interest act relatively independently. An example of a linear model is as follows:

$$y_i = a_{i1}y_1 + a_{i2}y_2 + \ldots + a_{iN}y_N + a_{ie1}u_1 + \ldots + a_{ieM}u_M + e \quad (8)$$

where: $y_i$ is the expression of the gene i, $u_j$'s represents the environmental factors involved in the biological process under study, and e is the noise factor. The model may or may not include time (t) as a factor. If the time factor is added, then the equation may consider the expression levels of all genes as well as the presence of environmental factors in a few past time samples. An example of a model describing environmental factors, time factors, and noise is as follows:

$$y_i(t) = f(y_1(t-1), y_1(t-2), \ldots, y_1(t-n_{a1}), y_2(t),$$
$$y_2(t-1), \ldots, y_2(t-n_{a2}), \ldots, y_N(t), y_N(t-1), \ldots,$$
$$y_N(t-n_{aN}), u_1(t), u_1(t-1), \ldots, u_1(t-n_{b1}), \ldots,$$
$$u_M(t), u_M(t-1), \ldots, u_M(t-n_{bM})) + e(t) \quad (9)$$

where: $n_{ai}$ and $n_{bj}$ are the degrees with respect to gene i and environmental factor j. In case of a linear model, the equation is reduced to:

$$y_i(t) = -a_{i11}y_1(t-1) - a_{i12}y_1(t-2) - \ldots - a_{i1n_{a1}}y_1(t-n_{a1}) -$$
$$a_{i20}y_2(t) - a_{i12}y_2(t-1) - \ldots - a_{i2n_{a2}}y_2(t-n_{a2}), \ldots, +$$
$$b u_1(t), u_1(t-1), \ldots, u_1(t-n_b), \ldots,$$
$$u_M(t), u_M(t-1), \ldots, u_M(t-n_{bM})) + e(t) \quad (10)$$

This type of analysis is an adaptation of the analysis used for linear Auto-Regressive exogenous (ARX) modeling. As described above, in some cases, variations of gene expression over time may be incorporated into the analysis. Thus, in an embodiment, the present invention comprises ARX modeling to relate genes in different consecutive time steps throughout the experiment.

For simplicity, a one-dimensional case is described. In the one dimensional case, the equations describe the situation where one gene is dynamically interacting with the environment. In an embodiment, extension of the equations to multi-dimensional case, where a number of genes are involved, may be performed. For the one dimensional case, the relation between the expression level of a gene at time t, y(t) is as:

$$y(t) + a_1 y(t-1) + \ldots + a_{na} y(t-n_a) = b_1 u(t-1) + \ldots + b_{nb} u(t-n_b) + e(t) \quad (11)$$

where y is gene expression (output), u is the environmental factor related to the biology study (i.e., exogenous input such as drug concentration), and e is the effect of other interfering environmental factors and experimental noise. The main objective is to determine the coefficients $a_1, a_2 \ldots$ and $a_{na}$ though which the model is completely defined. Defining θ as the vector of parameters as shown below:

$$\theta = (a_1 a_2 \ldots a_{n_a}, b_1, b_2, \ldots, b_{n_b}) \quad (12)$$

to predict the coefficients of equation (11), $\epsilon(t,\theta)$ may be defined as the prediction error as follows:

$$\epsilon(t,\theta) = y(t) - \hat{y}(t|\theta) \quad (13)$$

where $\hat{y}(t|\theta)$ is the predicted output given the set of parameters θ. Next, the prediction-error sequence may be processed through a stable linear filter L(q):

$$\epsilon_F(t,\theta) = L(q)\epsilon(t,\theta) \quad (14)$$

where q stands for an element of delay. Then, using $V_N(\theta,Z^N)$ as defined below, the total error (averaged over all data points) may be measured:

$$V_N(\theta, Z^N) = \frac{1}{N} \sum_{t=1}^{N} l(\varepsilon_F(t, \theta)) \quad (15)$$

where l(.) is any scalar-valued (positive) measure function (often defined as the square function). The parameter estimation is then defined as finding a set of parameters that minimizes the total error function (16).

$$\hat{\theta}_N = \hat{\theta}_N(Z^N) = \arg\min_{\theta \in D_M} V_N(\theta, Z^N) \quad (16)$$

To obtain these parameters, the least-squares method is applied. It may be assumed that $$\hat{y}(t|\theta) = \phi^T(t)\theta \quad (17)$$

where φ is the regression vector defined as shown by equation (18).

$$\phi(t) = [-y(t-1) - y(t-2) \ldots - y(t-n_a) u(t-1) \ldots u(t-n_b)]^T \quad (18)$$

With equation (18) the prediction error is defined by equation (19).

$$\epsilon(t,\theta) = y(t) - \phi^T(t)\theta \quad (19)$$

With $L(q)=1$ (i.e. identify filter), and $l(\epsilon)=\frac{1}{2}\epsilon^2$ (i.e. the square function), the total averaged error criterion function is defined by equation (20).

$$V_N(\theta, Z^N) = \frac{1}{N}\sum_{t=1}^{N}\frac{1}{2}[y(t) - \varphi^T(t)\theta]^2 \quad (20)$$

Equation (20) is the least-squares (LS) criterion for the linear regression and it can be minimized analytically to gives the equation (21) as the solution.

$$\hat{\theta}_N^{LS} = \arg\min \hat{V}_N(\theta, Z^N) = \left[\frac{1}{N}\sum_{t=1}^{N}\varphi(t)\varphi^T(t)\right]^{-1}\frac{1}{N}\sum_{t=1}^{N}\varphi(t)y(t) \quad (21)$$

Having calculated the set of parameters, the ARX model is completely defined and can be used for microarray time-series processing application. It is important to note that when the number of genes is very large, the ARX model can be created based on the independent components extracted from the previous part, i.e., instead of using individual gene expression as y(t)'s, independent components can be used y(t)'s in the ARX model.

Once a model describing the interrelationship between genes $y_1, y_2 \ldots y_n$, has been generated, it may be "pruned" to eliminate the weak links. In the pruning step, links that are statistically insignificant may be removed from the pathway. For example, for the linear case, the links ($a_{ij}$) may be tested for significance and links that are not significantly large may be removed. Such a process may be done in an iterative manner, in which the effect of removing a selected link or links is evaluated in terms of statistical fit. For example, if all the links originating or ending at a particular gene or environmental factor are set to zero, the gene or environmental factor is completely removed from the pathway.

Figure 4:
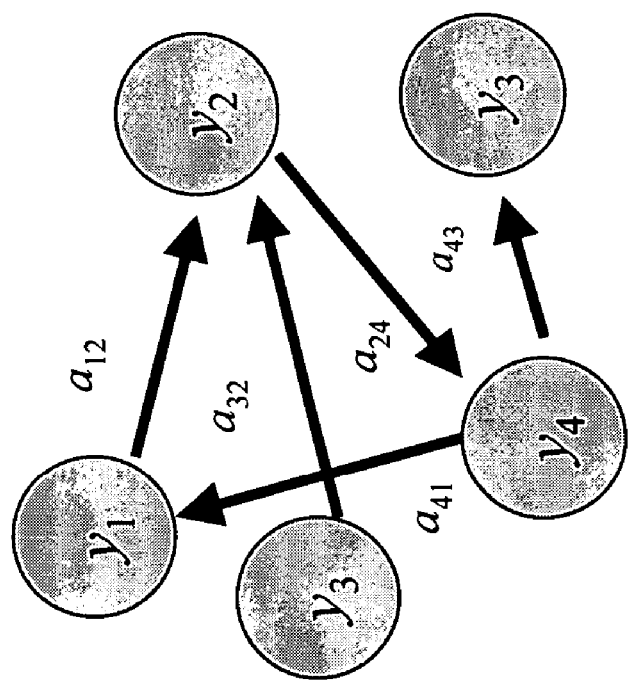
FIG. 4 shows a schematic depicting the interrelationship of four genes out of a larger network of genes in accordance with an embodiment of the present invention.
Figure 5A:
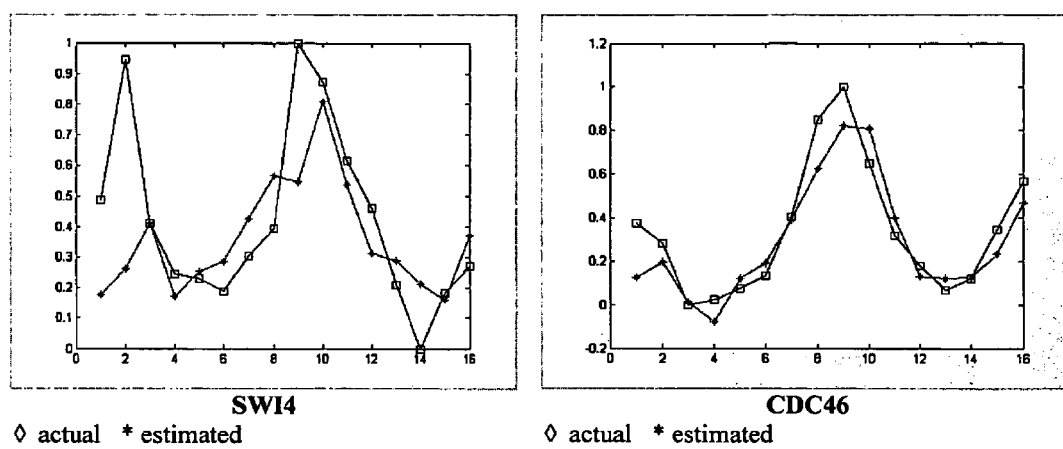
FIG. 5A shows the estimated and actual expression profiles for the SW14 and the CDC46 genes in early G1 phase, respectively.
Figure 5B:
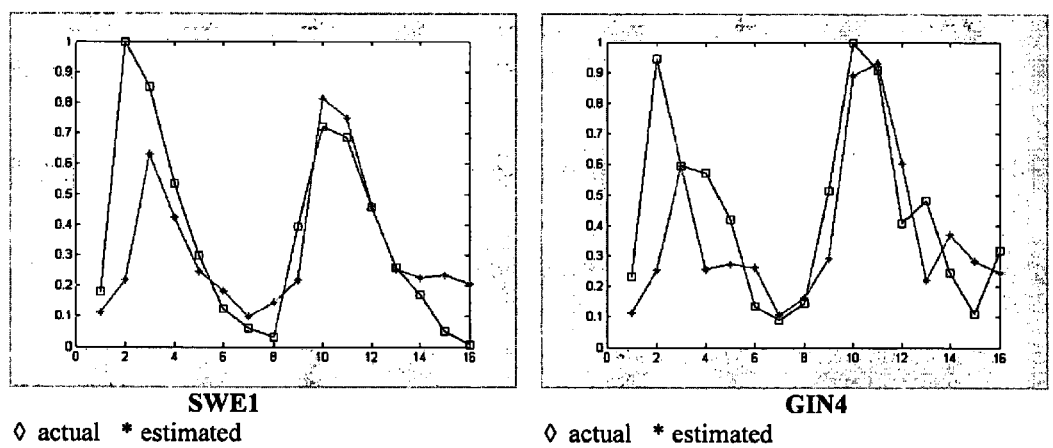
FIG. 5B shows the estimated and actual expression profiles for the SWE1 and the GIN4 genes in early G2 phase, respectively.
Figure 5C:
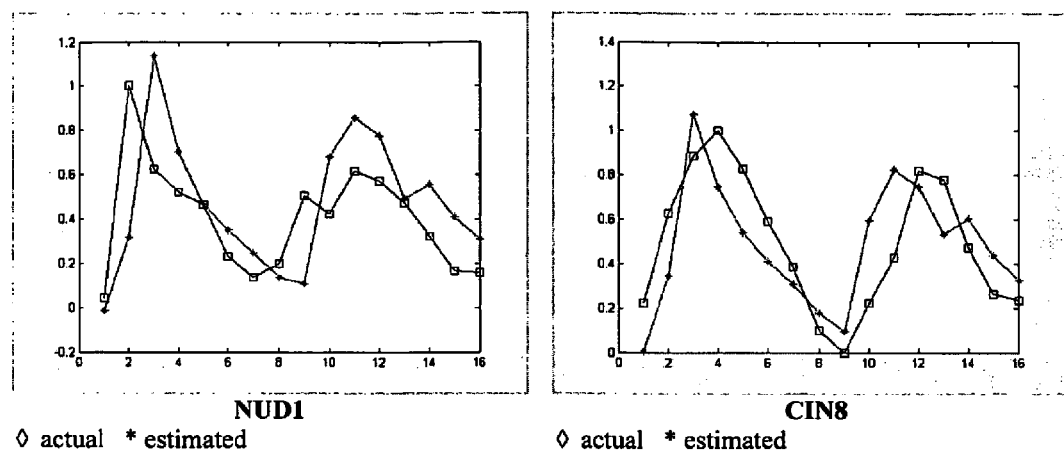
FIG. 5C shows the estimated and actual expression profiles for the NUD1 and the CIN8 genes in S phase, respectively.
Figure 5D:
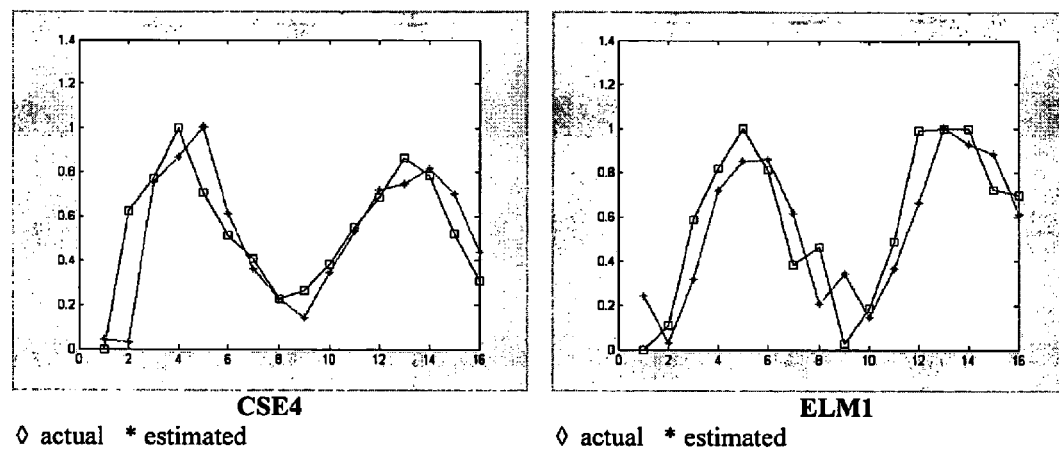
FIG. 5D shows the estimated and actual expression profiles for the CSE4 and the ELM1 genes in G2 phase, respectively.
Figure 5E:
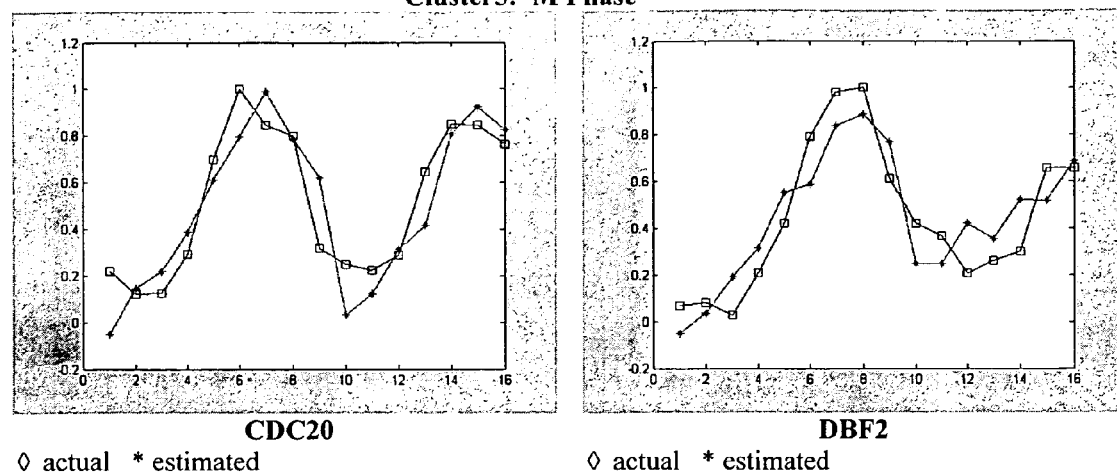
FIG. 5E shows the estimated and actual expression profiles for the CDC20 and the DBF2 genes in M phase, respectively.

After this pruning process, a simplified version of the pathway may be generated. In an embodiment, the simplified model may be visualized and understood as a graphical representation of the pathway. An example of a pathway after pruning, and assuming only genes (i.e., $y_1, y_2, y_3$, and $y_4$) and not environmental factors (e) is shown in FIG. 4. For example, in the model shown in FIG. 4, vectors $a_{21}$, $a_{23}$, and $a_{14}$ have been removed.

At the pruning state, the significance of the surviving links may be evaluated or "ranked" using a standard statistical test of fit such as T-test. In this analysis, links that play more important roles are ranked higher. In a visual representation, the stronger links with higher significance may be shown with thicker arrows.

In an embodiment, modifications of the formulation are used to provide a multi-variable model. In the p dimensional case of equation (1), where the expression levels of p genes at previous and present times are related to each other, $\theta$ and $\phi(t)$ are generalized as:

$$\theta = (A_1 \; A_2 \; \ldots \; A_n) \quad (22)$$

and $$\varphi(t) = [-Y(t-1) \; -Y(t-2) \; \ldots \; -Y(t-n)]^T \quad (23)$$

-continued where $$A_k = \begin{pmatrix} a_{k11} & a_{k12} & \ldots & a_{k1p} \\ a_{k21} & a_{k22} & & a_{k2p} \\ & & & \\ a_{kp1} & a_{kp2} & & a_{kpp} \end{pmatrix} \quad (24)$$

and $$Y(t) = [y_1(t) \; \ldots \; \ldots \; y_p(t)]^T. \quad (25)$$

The function $l(\epsilon)$ is modified as:

$$l(\varepsilon) = \frac{1}{2}\varepsilon^T \Lambda^{-1} \varepsilon \quad (26)$$

where $\Lambda$ is a symmetric positive semi definite p×p matrix that weighs the relative importance of the components of $\epsilon$. Also, for multi-variable case, $$V_N(\theta, Z^N) = h(Q_N(\theta, Z^N)) \quad (27)$$

where $$h(Q) = \frac{1}{2}\text{tr}(Q\Lambda^{-1}) \quad (28)$$

and, $$Q_N(\theta, Z^N) = \frac{1}{N}\sum_{t=1}^{N}\varepsilon(t, \theta)\varepsilon^T(t, \theta). \quad (29)$$

For a p dimensional case, the LS criterion takes the form shown as equation (30).

$$V_N(\theta, Z^N) = \frac{1}{N}\sum_{t=1}^{N}\frac{1}{2}[y(t) - \varphi^T(t)\theta]^T \Lambda^{-1} [y(t) - \varphi^T(t)\theta] \quad (30)$$

This leads to the following equation (31) to find the model parameters in multidimensional cases.

$$\hat{\theta}_N^{LS} = \left[\frac{1}{N}\sum_{t=1}^{N}\varphi(t)\Lambda^{-1}\varphi^T(t)\right]^{-1}\frac{1}{N}\sum_{t=1}^{N}\varphi(t)\Lambda^{-1}y(t) \quad (31)$$

For example, in an embodiment, microarray gene expression data for the budding yeast *S. Cerevisiae* may be analyzed to identify the gene expression pattern during the cell cycle of the budding yeast *S. Cerevisiae*. Yeast cells may be arrested in the late G1 stage of the cell cycle by raising the temperature to 37° C., and the cell cycle reinitiated by shifting cells to 25° C., thereby obtaining a synchronous cell culture. Cells may be harvested over the course of multiple cell cycles. Genes which have been activated in each phase of cell cycle have been previously identified (Cho et al., *Molecular Cell*, 2:65-73, 1998). Thus, it is known that *S. Cerevisiae* genes can be divided into five groups, according to the stage in which the gene is expressed. The first cluster includes genes active in early G1, the second cluster includes genes which are active in late G1, and the third, the fourth and fifth clusters correspond to the genes which are activated in S, G2 and M phases of the cell cycle, respectively.

The main purpose of applying the ARX model to the data is to discover the effect that each gene has on itself and other genes in the next time steps. For this reason, gene expression is considered to be the output. For example, in the study of gene expression in yeast assayed at various points in the cell cycle, there will be multiple outputs (independent components) and no exogenous inputs (since there is no perturbation). This means that there are five outputs (one for each cell cycle phase), and u(t) may be set to zero for all time points. In an embodiment, the model parameters (i.e., coefficients) may be estimated using the independent component as the training set. To determine how well the resulting model relates the expression level of each individual gene to the other genes, the developed model may be used to predict the expression level of genes from each cluster. The predicted and true values of the expression levels for these genes are compared in FIG. 5, panels 5A, 5B, 5C, 5D, and 5E. As can be seen, the model can accurately predict the expression levels.

Systems for Analysis of Arrays

In an embodiment, the present invention provides systems for carrying out array analysis. Thus, in an embodiment, the present invention comprises a computer-readable medium on which is encoded programming code for analyzing gene expression from a plurality of data points comprising using iterative independent component analysis to cluster the data into independent groups.

Also in an embodiment, the present invention may comprise a computer-readable medium on which is encoded programming code for analyzing gene expression comprising code for: (a) removing noise from the data; (b) using an iterative independent component analysis to cluster data comprising a plurality of data points into n independent groups; and (c) determining cross-correlation between at least two genes within a group, wherein cross-correlation may comprise a dependency of expression of one gene in the group upon the expression of a second gene in the group.

Embodiments of computer-readable media include, but are not limited to, an electronic, optical, magnetic, or other storage device capable of providing a processor with computer-readable instructions. Other examples of suitable media include, but are not limited to, a floppy disk, CD-ROM, magnetic disk, memory chip, ROM, RAM, an ASIC, a configured processor, all optical media, or all magnetic tape or other magnetic media. The instructions may comprise code from any computer-programming language, including, for example, C, VISUAL C#®, VISUAL BASIC®, VISUAL FOXPRO®, Java, and JavaScript.

The present invention further comprises systems using the computer-readable medium comprising iterative independent component analysis for gene expression array analysis. Thus, as described above, the present invention comprises a system for analyzing gene expression comprising using iterative independent component analysis (ICA) to identify an optimum number of independent clusters into which data comprising a plurality of measured signals may be grouped. In an embodiment, the system comprises a computer and programming code embodied on a computer-readable medium. Thus, in an embodiment, the computer-readable medium on which is encoded programming code for analyzing gene expression applies iterative independent component analysis (ICA) to data comprising a plurality of measured signals to identify an optimum number of independent clusters into which the data may be grouped.

As described above, the system may comprise an imaging unit as well as a means for the user to interact with the system as the analysis proceeds. Thus, in an embodiment, the present invention further comprises a unit for collecting and/or compiling data from said plurality of measured signals and transmitting said data to said computer, and a unit for transmitting the results of said analysis to a user.

The systems of the present invention are designed for high-throughput analysis of DNA hybridization data. Thus, in an embodiment, the plurality of measured signals comprise a plurality of known DNA sequences hybridized to mRNA isolated from at least one cell type.

Also described above, in an embodiment, the system utilizes an iterative ICA to provide an optimal number of independent gene groups that explain the gene expression profiles being measured. In an embodiment, the number of gene groups, n, is estimated as a preset number, $n_0$. The data may then be evaluated by increasing the number of groups from $n_0$ and performing an iterative analysis of the relative fit of the data using $n_0$ as compared to the new value of n. In an embodiment, the number of groups are increased incrementally by 1 group for each evaluation, such that the number of groups increases at each step from $n_0$, to $n_0+1$, to $n_0+2$, until the optimum number of groups ($n_{opt}$) is determined. Also, in an embodiment, the system comprises hierarchical ICA such that the complexity of the computational analysis is reduced as the analysis proceeds, by removing inputs that have been described at earlier stages of the analysis from the set of data points still remaining to be characterized. The system may also comprise determining if there is a cross-correlation between at least two data signals within a cluster group, wherein a positive cross-correlation comprises the situation in which the expression of one gene in the group is statistically correlated with the expression of a second gene in the same group. In an embodiment, expression of one of the genes may be dependent upon expression of the other gene.

Figure 6:
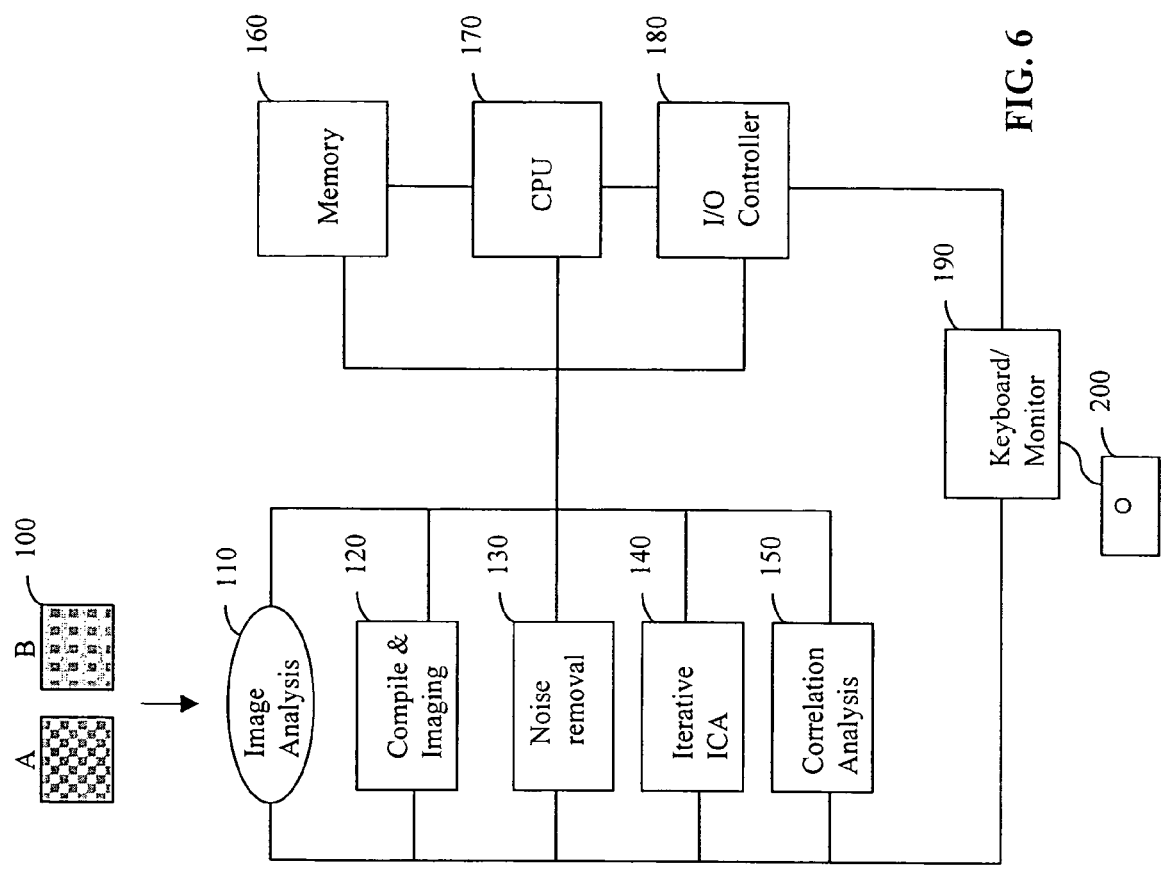
FIG. 6 shows a schematic diagram of a system for array analysis in accordance with an embodiment of the present invention.

FIG. 6 shows an embodiment of the flow of information in a system comprising the software of the present invention. As used herein, a computer processor or CPU may include, for example, digital logic processors capable of processing input, executing algorithms, and generating output as necessary in response to the inputs received from the touch-sensitive input device. Such processors may include a microprocessor, such as an ASIC, and state machines. Such processors include, or may be in communication with, media, for example computer-readable media, which stores instructions that, when executed by the processor, cause the processor to perform the steps described herein.

Thus, in an embodiment, the starting point may comprise the image generated from a gene expression array or arrays (100). Alternatively, as for example where a radiolabeled probe is used, the input data may comprise a matrix corresponding to the amount of probe detected at each address. The data may be processed using an imaging system such as a imaging system commercially available from General Electric Corporation (110), or by other techniques, such as X-ray imaging or the like. The imaging system used may be custom-designed, or may be one of a number of commercially available packages.

Once the data has been collected (i.e., using the imaging system or other type of data collection system), it may be compiled (120) and/or transformed if necessary using any standard spreadsheet software such as Microsoft Excel, FOXPRO®, Lotus, or the like. In an embodiment, the data are entered into the system for each experiment. Alternatively, data from previous runs are stored in the computer memory (160) and used as required.

At each point in the analysis, the user may input instructions via a keyboard (190), floppy disk, remote access (e.g., via the internet) (200), or other access means. The user may enter instructions including options for the run, how reports should be printed out, and the like. Also, at each step in the analysis, the data may be stored in the computer using a storage device common in the art such as disks, drives or memory (160). As is understood in the art, the processor (170) and I/O controller (180) are required for multiple aspects of computer function. Also, in a embodiment, there may be more than one processor.

The data may also be processed to remove noise (130) as described herein. In some cases, the user, via the keyboard (190), floppy disk, or remote access (200), may want to input variables or constraints for the analysis, as for example, the threshold for determining noise.

In the next step, iterative ICA (140) is performed as described above. In some cases, the user may want to input variables or constraints for the analysis, as for example, where the number of gene groups is known. Also, the user may choose which type of ICA software may be employed for the analysis. Examples of commercially available processing software suitable for microarray analysis include, but are not limited to MATLAB® (The MathWorks, Natick, Mass.), and SAS (SAS Institute, Inc., Cary, N.C.). For example, in one embodiment of the present invention, a prototype was coded using MATLAB® (without using the MATLAB® bioinformatics toolbox or any other MATLAB® function specialized for microarray processing). Thus, as described above, in some situations, FastICA may be the software of choice. Other situations, however, may require a more rigorous ICA program to be used.

Finally, the clusters defined by ICA can be correlated to a biological response function and correlation analysis (150) (e.g., ARX analysis) for genes within the cluster may be performed. Again, the user may want to input variables or constraints for the analysis, as for example, a limit for determining the significance of links between genes.

EXAMPLES

Example 1

Measurement of Gene Expression by Array Analysis for Genes Related to Bone Healing FastICA (available from Helsinki University of Technology) implemented in MATLAB® 6.0 (The Mathworks, Inc., Natick, Mass.) was used for the analysis of gene expression data relating to bone healing. Although not as accurate as the traditional ICA methods, FastICA provides a much faster technique when large datasets are used. The hardware was a 1 GHz AMD ATHLON PROCESSOR® with 768 Mb memory. The input data was a series of four microarray measurements for the expression levels of genes of young rats during the bone fracture healing process. The data also included a starting non-fracture measurement.

The largest data set included 8,799 data points. For the removal of noise, the data from the control (the non-fracture reading) was subtracted from each subsequent data point (after fracture and during the healing process). Using a simple (i.e., non-optimized) filtering technique, series with changes less than 100 linear units of expression level were discarded. In the matrix array analyzer used (AFFYMETRIX®), expression levels below 100 are believed to be caused by machine noise and other sources of noise. Subtraction of noise left 4,315 series to consider. Due to the use of auto-correlation techniques for filtering (as discussed above) the filtering process is optimal and eliminates the noise-like patterns that have no significant biological basis.

ICA reduced the 4,315 components down to 530 independent components. As described above, the results of the modified FastICA algorithm (which is made hierarchical and dynamic) yields three matrices. The hierarchical nature of the revised version assets that the algorithm can start with n−1 independent components and add a new component based on the given signals. The first matrix defined by ICA contains a set of basis functions (i.e., s(t) in formulas above). The second matrix contains the mixing matrix (i.e., A in the formulas above), and the third matrix contains the separating matrix (W). Obtaining the actual independent components (signals) was done using the equations given above.

For this experiment, the sample size in time was K=4 (four time readings per gene) and the mean of the measured signals, x(t), was subtracted out. Subtracting out the means makes the figures easier to read and eliminates the chances of over-weighting a gene due to baselines. The ICA signal components, s(t), were then plotted. Some of the components for this experiment are shown in FIG. 2, where the vertical axis is the amplitude of the normalized expression level and the horizontal axis is time. It can be seen that for this dataset, each of the independent components shows a different expression profile.

The next task was to determine what genes make up a given pathway. For this data, the maximum mixing coefficient was over 2,000 and the minimum mixing coefficient was under −2,100. The number of genes identified as being part of the identified group depends in part on the cutoff value used. If values of 20% of the maximum or minimum were chosen, the number of contributing genes was 750. Choosing a cutoff value of 5% reduced the count to 94. The 94 genes that make up pathway number 1, are listed in Table 1, below.

FIG. 3 shows a composite of all 94 signals for these genes. Although the figure is too compressed in some regions to show correlations for many of the genes, some of the outer sequences can be seen to have highly correlated (or anti-correlated) expression profiles. The gene names used in Table 1 are the standard names used in public databases such as the data base available as the rat genome database at the Medical College of Wisconsin website.

TABLE 1

| Genes Identified as Group 1 by ICA | |
|---|---|
| Gene ID | Gene Name |
| 125 | rc_AA819708_s_at |
| 192 | M24604_g_at |
| 238 | rc_AA875107_at |
| 282 | rc_AA899854_at |
| 287 | rc_AA944397_at |
| 309 | rc_AI229620_s_at |
| 384 | AF048687_s_at |
| 424 | D14014_at |
| 600 | L03294_at |
| 611 | L24896_s_at |
| 622 | J02585_at |
| 683 | U53922_at |
| 714 | X06827_g_at |
| 734 | U53855_at |
| 769 | D00680_at |
| 788 | M14050_s_at |
| 947 | X53363cds_s_at |

TABLE 1-continued

Genes Identified as Group 1 by ICA

| Gene ID | Gene Name |
|---|---|
| 956 | X62086mRNA_s_at |
| 992 | Y13336cds_g_at |
| 1196 | AB018049_s_at |
| 1630 | AJ001929_s_at |
| 1668 | AJ009698_at |
| 1879 | D30804_at |
| 1906 | D42116_s_at |
| 1907 | D42137exon_s_at |
| 1916 | D45247_g_at |
| 1964 | D85183_s_at |
| 1966 | D85435_g_at |
| 2075 | L10652_at |
| 2110 | L14462_at |
| 2144 | L27843_s_at |
| 2151 | L31394exon_s_at |
| 2231 | M22340cds#1_s_at |
| 2459 | S61868_g_at |
| 2472 | S63233_g_at |
| 2512 | S69315_at |
| 2518 | S69874_s_at |
| 2525 | S71021_s_at |
| 2590 | S78217_s_at |
| 2591 | S78218_at |
| 2667 | U02506UTR#1_s_at |
| 2998 | X14323cds_at |
| 3098 | X59736mRNA_at |
| 3123 | X62145cds_g_at |
| 3144 | X62951mRNA_s_at |
| 3223 | X90475cds_at |
| 3431 | M74494_g_at |
| 3654 | L19180_at |
| 3815 | X72914_at |
| 4133 | AB012234_at |
| 4171 | S54008_i_at |
| 4245 | M15882_g_at |
| 4523 | rc_AI639060_at |
| 5058 | rc_AA800745_at |
| 5138 | rc_AA945611_at |
| 5273 | rc_AI010480_at |
| 5362 | rc_AI059963_at |
| 5470 | rc_AI102031_g_at |
| 5495 | rc_AI103957_at |
| 5562 | rc_AI172162_at |
| 5563 | rc_AI172247_at |
| 5596 | rc_AI176589_g_at |
| 5637 | rc_AI179610_at |
| 5717 | rc_AI232477_s_at |
| 5797 | M25073_at |
| 5820 | K02815_s_at |
| 5967 | J04993_at |
| 6177 | U24150_at |
| 6456 | X52840_r_at |
| 6534 | D43623_g_at |
| 6582 | D10874_g_at |
| 6603 | X94551_at |
| 6719 | D78308_g_at |
| 6721 | D78359_at |
| 6749 | J04793_at |
| 6868 | AF016296_at |
| 7060 | rc_AA859536_at |
| 7071 | rc_AA859581_at |
| 7290 | rc_AA874848_s_at |
| 7499 | rc_AA875665_g_at |
| 7607 | rc_AA685178_at |
| 7618 | rc_AA891054_at |
| 7630 | rc_AA891171_s_at |
| 7655 | rc_AA891302_g_at |
| 7753 | rc_AA891797_at |
| 7755 | rc_AA891800_g_at |
| 7927 | rc_AA892388_at |
| 8266 | rc_AA893846_at |
| 8340 | rc_AA894207_g_at |
| 8396 | rc_AA799423_at |
| 8585 | rc_AA799861_g_at |
| 8622 | rc_AA800029_at |
| 8668 | rc_AA800250_at |
| 8698 | rc_AA800566_g_at |

Example 2

Identification of Genes within Independent Component Groups for *S. Cerevisiae*

In this example, microarray gene expression data of the budding yeast *S. Cerevisiae* was analyzed to identify the mRNA transcript levels during the cell cycle of the budding yeast *S. Cerevisiae*. To obtain synchronous yeast culture, cdc28-13 yeast cells were arrested in late G1 by raising the temperature to 37° C., and then reinitiating the cell cycle by shifting cells to 25° C. Cells were collected at 17 time points taken at 10 min intervals, covering nearly two cell cycles (Cho et al, *Molecular Cell,* 2:65-73, 1998). Genes which have been activated in each phase of cell cycle (Early G1 phase, Late G1 phase, S phase, G2 phase or M phase) have been previously identified (Cho et al., *Molecular Cell,* 2:65-73, 1998) based on the functionality of the genes in each phase. Thus, it is known that the genes involved in the cell cycle process can be divided into five clusters depending upon the stage in which they are active.

ARX was applied to the data to discover the effect that each gene has on itself and other genes in the next phase of the cell cycle. As described above, in this analysis, gene expression is considered to be the output of the ARX model and there are no inputs (since there is no perturbation). Since the number of genes was large, each cluster was assumed to be one independent component, and the ARX model was trained to relate the independent components of clusters to each other.

The model parameters (i.e., coefficients) were estimated using the independent component as the training set. In order to see how well the resulting model could dynamically relate the expression level of each individual gene to the other genes, the model was used to predict the expression level of individual genes from each cluster. The predicted and true values of the expression levels for these genes are compared in FIG. 5, panels A-E. As can be seen, the model predicted the expression level accurately. The full gene names for the genes described in FIG. 5 can be found in Cho et al., 1998.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

What is claimed is:

1. A system for analyzing gene expression for at least one cell type comprising:
   a computer-readable medium; and
   a processor in communication with the computer-readable medium, the processor configured to:
     receive compiled data comprising a plurality of measured gene expression signals;
     analyze the compiled data using iterative independent component analysis (ICA) to identify an optimum number of independent clusters into which the compiled data may be grouped; and
output results of the analysis.

2. The system of claim 1, wherein the plurality of measured gene expression signals comprise data obtained by hybridization of mRNA from at least one cell type to DNA sequences from a plurality of known genes.

3. The system of claim 1, wherein the processor is further configured to correlate the number of independent clusters to a pattern of gene expression for at least one cell type.

4. The system of claim 1, wherein the processor is further configured to correlate at least one of the measured gene expression signals to experimental noise and to at least one underlying source generating the measured gene expression signal.

5. The system of claim 1, wherein the processor is further configured to:
correlate at least one of the measured gene expression signals, x, to experimental noise, n, and to at least one underlying source, s, and
generate a signal, as a function of time, t, such that: $x(t)=f(s(t))+n(t)$.

6. The system of claim 1, wherein the processor is further configured to use an algorithm that yields three matrices: (i) a set of sources $(s_1(t), s_2(t) \ldots s_M(t))$; (ii) a mixing matrix, and (iii) a separating matrix, wherein the separating matrix is the inverse of the mixing matrix.

7. The system of claim 1, wherein the processor is further configured to normalize the variance of the compiled data.

8. The system of claim 1, wherein the optimum number of independent clusters is n, and is initially estimated as a preset number, $n_0$.

9. The system of claim 8, wherein the processor is further configured to: evaluate the compiled data by sequentially increasing a number of independent clusters from a minimum number, $n_0$, and
determine a relative fit of the compiled data using $n_0$ as compared to a new value of n.

10. The system of claim 9, wherein the processor is further configured to increase the number of independent clusters incrementally by one for each iteration, such that the number of independent clusters into which the compiled data may be grouped increases at each step from $n_0$, until an optimum number of independent clusters ($n_{opt}$) is determined.

11. The system of claim 1, wherein the processor is further configured to perform dynamic ICA to generate a model that at least in part describes how the gene expression signals change over time.

12. The system of claim 1, wherein the processor is further configured to perform hierarchical ICA, such that a complexity of the iterative ICA is reduced as the analysis proceeds by removing data that has been described at earlier stages of the analysis from a set of compiled data points still remaining to be characterized.

13. The system of claim 1, wherein the processor is further configured to determine a relationship between at least two measured gene expression signals within a single cluster group, or between at least two measured gene expression signals in at least two separate cluster groups.

14. The system of claim 13, wherein the processor is further configured to determine if there is a cross-correlation between the at least two measured gene expression signals within the single cluster group, or between the at least two measured gene expression signals in the at least two separate cluster groups, wherein a positive cross-correlation comprises a situation in which one gene expression signal is statistically correlated with a second gene expression signal.

15. The system of claim 13, wherein the processor is further configured to determine the relationship between at least two independent clusters as a model describing relative levels of gene expression for the independent clusters.

16. The system of claim 13, wherein the processor is further configured to determine the relationship between the at least two measured gene expression signals within the single cluster group, or between the at least two measured gene expression signals in the at least two separate cluster groups as a model describing relative levels of expression for the individual genes.

17. The system of claim 13, wherein the processor is further configured to perform autoregressive exogenous modeling based on the at least two measured gene expression signals within the single cluster group or the at least two measured gene expression signals in the at least two separate cluster groups.

18. The system of claim 13, wherein the relationship between the at least two measured gene expression signals within the single cluster group, or between the at least two measured gene expression signals in the at least two separate cluster groups is defined by the expression $y_i=f(y_1, y_2, \ldots y_N, u_1, \ldots u_M)+e$, where $y_1, y_2 \ldots y_N$, is the expression of individual genes or clusters 1, 2, ... N; $u_1, u_2 \ldots u_M$, corresponds to environmental factors 1, 2 ... M, and experimental noise is defined by e, and f is a linear or a non-linear function.

19. The system of claim 18, wherein the processor is further configured to determine individual coefficients for each of the individual genes or clusters by minimizing the prediction error for each of the coefficients.

20. The system of claim 13, wherein the processor is further configured to determine the relationship between the at least two measured gene expression signals within the single cluster group, or between the at least two measured gene expression signals in the at least two separate cluster groups by removing statistically insignificant links from a model describing the relationship between the at least two measured gene expression signals within the single cluster group, or between the at least two measured gene expression signals in the at least two separate cluster groups.

21. A system for analyzing gene expression for at least one cell type comprising:
a computer-readable medium; and
a processor in communication with the computer-readable medium, the processor configured to:
analyze data using iterative independent component analysis (ICA), wherein the data comprises a plurality of measured gene expression signals;
identify an optimum number of independent clusters into which the data may be grouped;
determine a relationship between at least two measured gene expression signals within a single cluster group, or between at least two measured gene expression signals in at least two separate cluster groups; and
output results of the iterative ICA and the relationship.

22. The system of claim 21, wherein the processor is further configured to perform autoregressive exogenous modeling based on the at least two measured gene expression signals within the single cluster group or the at least two measured gene expression signals in the at least two separate cluster groups.

23. The system of claim 21, wherein the processor is further configured to correlate the optimum number of independent clusters into which the data may be grouped to a pattern of gene expression for at least one cell type.

24. The system of claim 21, wherein the processor is further configured to correlate at least one of the measured gene expression signals to experimental noise and at least one underlying source generating the measured gene expression signal.

25. The system of claim 21, wherein the processor is further configured to:
correlate at least one of the measured gene expression signals, x, to experimental noise, n, and to at least one underlying source, s, and
generate a signal, as a function of time, t, such that: $x(t)=f(s(t))+n(t)$.

26. The system of claim 21, wherein the processor is further configured to use an algorithm that yields three matrices: (i) a set of sources $(s_1(t), s_2(t) \ldots s_M(t))$; (ii) a mixing matrix, and (iii) a separating matrix, wherein the separating matrix is the inverse of the mixing matrix.

27. The system of claim 21, wherein the optimum number of independent clusters is n, and is initially estimated as a preset number, $n_0$.

28. The system of claim 21, wherein the processor is further configured to:
evaluate the data by sequentially increasing the number of independent clusters from a minimum number, $n_0$, and determine a relative fit of the data using $n_0$ as compared to a new value of n.

29. The system of claim 28, wherein the processor is configured to increase a number of independent clusters incrementally by one for each evaluation, such that the number of independent clusters into which the data may be grouped increases at each step from $n_0$, until an optimum number of independent clusters ($n_{opt}$) is determined.

30. The system of claim 21, wherein the processor is further configured to perform at least one of dynamic ICA to generate a model that at least in part describes how the gene expression signals change over time, or hierarchical ICA, such that a complexity of the iterative ICA is reduced as the analysis proceeds by removing data that has been described at earlier stages of the analysis from the set of data points still remaining to be characterized.

31. The system of claim 21, wherein the processor is further configured to determine if there is a cross-correlation between the at least two measured gene expression signals within the single cluster group, or between the at least two measured gene expression signals in the at least two separate cluster groups, wherein a positive cross-correlation comprises a situation in which one gene expression signal is statistically correlated with a second gene expression signal.

32. The system of claim 21, wherein the processor is further configured to determine the relationship between at least two independent clusters as a mathematical model describing relative levels of expression for the independent clusters.

33. The system of claim 21, wherein the processor is further configured to determine the relationship between the at least two measured gene expression signals within the single cluster group, or between the at least two measured gene expression signals in the at least two separate cluster groups as a mathematical model describing relative levels of expression for individual genes.

34. The system of claim 21, wherein the relationship between the at least two measured gene expression signals within the single cluster group, or between the at least two measured gene expression signals in the at least two separate cluster groups is defined by the expression $y_i=f(y_1, y_2, \ldots y_N, u_1, \ldots u_M)+e$, where $y_1, y_2 \ldots y_N$, is the expression of individual genes or clusters 1, 2, ... N; $u_1, u_2 \ldots u_M$, corresponds to environmental factors 1, 2 ... M, and experimental noise is defined by e, and f is a linear or a non-linear function.

35. The system of claim 21, wherein the processor is configured to determine individual coefficients for each of the genes or clusters by minimizing a prediction error for a set of coefficients.

36. The system of claim 21, wherein the processor is configured to determine the relationship between at least two measured signals by removing statistically insignificant links from a model describing the relationship between the at least two measured gene expression signals within the single cluster group, or between the at least two measured gene expression signals in the at least two separate cluster groups.

37. A non-transitory computer-readable medium on which is encoded program code for analyzing gene expression from a plurality of data, the programming code comprises:
program code for compiling the plurality of data,
program code for analyzing the compiled data using iterative independent component analysis (ICA), wherein the program code for analyzing comprises program code for identifying an optimum number of independent clusters into which the compiled data may be grouped, and
program code for transforming the results of the analysis to a form to be available to a user.

38. The non-transitory computer readable medium of claim 37, further comprising program code for determining a relationship between at least two measured gene expression signals within a single cluster group, or between at least two measured gene expression signals in at least two separate cluster groups.

39. The non-transitory computer readable medium of claim 38, wherein the program code for determining the relationship comprises program code for determining the relationship between the at least two genes or the at least two clusters using autoregressive exogenous modeling.

40. The non-transitory computer-readable medium of claim 38, wherein the relationship between the at least two measured gene expression signals within the single cluster group, or between the at least two measured gene expression signals in the at least two separate cluster groups is defined by the expression $y_i=f(y_1, y_2, \ldots y_N, u_1, \ldots u_M)+e$, where $y_1, y_2 \ldots y_N$, is the expression of individual genes or clusters 1, 2, ... N; $u_1, u_2 \ldots u_M$, corresponds to environmental factors 1, 2 ... M, and experimental noise is defined by e, and f is a linear or a non-linear function.

41. The non-transitory computer-readable medium of claim 37, wherein the program code for analyzing the compiled data further comprises:
program code for correlating at least one of the measured gene expression signals, x, to experimental noise, n, and to at least one underlying source, s, and
program code for generating a signal, as a function of time, t, such that: $x(t)=f(s(t))+n(t)$.

42. The non-transitory computer-readable medium of claim 37, wherein the program code for analyzing the compiled data further comprises an algorithm that yields three matrices: (i) a set of sources $(s_1(t), s_2(t) \ldots s_M(t))$; (ii) a mixing matrix, and (iii) a separating matrix, wherein the separating matrix is the inverse of the mixing matrix.

* * * * *